US011826113B2

(12) United States Patent
Bakirtzian et al.

(10) Patent No.: US 11,826,113 B2
(45) Date of Patent: Nov. 28, 2023

(54) SYSTEMS AND METHODS TO COMPUTE A SUBLUXATION BETWEEN TWO BONES

(71) Applicant: INTELLIJOINT SURGICAL INC., Kitchener (CA)

(72) Inventors: Armen Garo Bakirtzian, Kitchener (CA); Andre Novomir Hladio, Waterloo (CA); Richard Tyler Fanson, Stoney Creek (CA); Eric Ryterski, Louisville, CO (US)

(73) Assignee: Intellijoint Surgical Inc., Kitchener (CA)

( * ) Notice: Subject to any disclaimer, the term of this patent is extended or adjusted under 35 U.S.C. 154(b) by 0 days.

(21) Appl. No.: 18/109,174

(22) Filed: Feb. 13, 2023

(65) Prior Publication Data

US 2023/0190387 A1    Jun. 22, 2023

Related U.S. Application Data

(63) Continuation of application No. 17/115,684, filed on Dec. 8, 2020, now Pat. No. 11,589,930, which is a
(Continued)

(51) Int. Cl.
*A61B 34/20* (2016.01)
*A61B 5/00* (2006.01)
(Continued)

(52) U.S. Cl.
CPC ............ *A61B 34/20* (2016.02); *A61B 5/0077* (2013.01); *A61B 5/061* (2013.01); *A61B 5/1072* (2013.01);
(Continued)

(58) Field of Classification Search
CPC .................................................. A61F 2/4607
See application file for complete search history.

(56) References Cited

U.S. PATENT DOCUMENTS

| 4,522,196 A | 6/1985 | Cunningham et al. |
| 4,994,064 A | 2/1991 | Aboczky |

(Continued)

FOREIGN PATENT DOCUMENTS

| CN | 101641044 A | 2/2010 |
| CN | 102196782 A | 9/2011 |

(Continued)

OTHER PUBLICATIONS

Search Report for Corresponding Chinese Patent Application No. 201910642969.1; dated Oct. 25, 2021; 3 Pages; Chinese Translation.

(Continued)

*Primary Examiner* — Sameh R Boles

(57) ABSTRACT

Systems, methods and a sensor alignment mechanism are disclosed for medical navigational guidance systems. In one example, a system to make sterile a non-sterile optical sensor for use in navigational guidance during surgery includes a sterile drape having an optically transparent window to drape the optical sensor in a sterile barrier and a sensor alignment mechanism. The alignment mechanism secures the sensor through the drape in alignment with the window without breaching the sterile barrier and facilitates adjustment of the orientation of the optical sensor. The optical sensor may be aligned to view a surgical site when the alignment mechanism, assembled with the sterile drape and optical sensor, is attached to a bone. The alignment mechanism may be a lockable ball joint and facilitate orientation of the sensor in at least two degrees of freedom. A quick connect mechanism may couple the alignment mechanism to the bone.

12 Claims, 14 Drawing Sheets

Related U.S. Application Data continuation of application No. 16/242,509, filed on Jan. 8, 2019, now Pat. No. 10,881,468, which is a continuation of application No. 15/497,721, filed on Apr. 26, 2017, now Pat. No. 10,194,996, which is a continuation of application No. 14/990,179, filed on Jan. 7, 2016, now Pat. No. 9,655,749, which is a continuation of application No. 13/833,181, filed on Mar. 15, 2013, now Pat. No. 9,247,998.

(51) Int. Cl.
  A61B 90/00 (2016.01)
  A61B 5/107 (2006.01)
  A61B 5/11 (2006.01)
  A61B 90/70 (2016.01)
  A61B 5/06 (2006.01)
  A61F 2/46 (2006.01)
  A61B 34/00 (2016.01)
  A61B 17/90 (2006.01)
  A61B 17/56 (2006.01)

(52) U.S. Cl.
  CPC .......... *A61B 5/1079* (2013.01); *A61B 5/1121* (2013.01); *A61B 5/1127* (2013.01); *A61B 5/4571* (2013.01); *A61B 90/06* (2016.02); *A61B 90/70* (2016.02); *A61F 2/4607* (2013.01); *A61B 17/90* (2021.08); *A61B 2017/567* (2013.01); *A61B 2034/2055* (2016.02); *A61B 2034/252* (2016.02); *A61B 2090/067* (2016.02); *A61B 2090/3983* (2016.02); *A61B 2090/3991* (2016.02); *A61F 2/4657* (2013.01); *A61F 2002/4668* (2013.01)

(56) References Cited

U.S. PATENT DOCUMENTS

| | | | |
|---|---|---|---|
| 5,122,145 A | 6/1992 | Fishbane |
| 5,141,512 A | 8/1992 | Farmer et al. |
| 5,227,985 A | 7/1993 | DeMenthon |
| 5,249,581 A | 10/1993 | Horbal et al. |
| 5,433,221 A | 7/1995 | Adair |
| 5,480,439 A | 1/1996 | Bisek et al. |
| 5,591,119 A | 1/1997 | Adair |
| 5,611,353 A | 3/1997 | Dance et al. |
| 5,700,268 A | 12/1997 | Bertin |
| 5,772,610 A | 6/1998 | McGorry et al. |
| 5,807,252 A | 9/1998 | Hassfeld et al. |
| 5,854,843 A | 12/1998 | Jacknin et al. |
| 5,880,976 A | 3/1999 | DiGioia, III et al. |
| 5,956,660 A | 9/1999 | Neumann |
| 5,966,827 A | 10/1999 | Horvath et al. |
| 6,009,189 A | 12/1999 | Schaack |
| 6,061,644 A | 5/2000 | Leis |
| 6,161,032 A | 12/2000 | Acker |
| 6,395,005 B1 | 5/2002 | Lovell |
| 6,450,978 B1 | 9/2002 | Brosseau et al. |
| 6,529,765 B1 | 3/2003 | Franck et al. |
| 6,607,487 B2 | 8/2003 | Chang et al. |
| 6,692,447 B1 | 2/2004 | Picard |
| 6,711,431 B2 | 3/2004 | Sarin et al. |
| 6,917,827 B2 | 7/2005 | Kienzle, III |
| 6,925,339 B2 | 8/2005 | Grimm et al. |
| 6,978,167 B2 | 12/2005 | Dekel et al. |
| 6,988,009 B2 | 1/2006 | Grimm et al. |
| 7,001,346 B2 | 2/2006 | White |
| 7,130,676 B2 | 10/2006 | Barrick |
| 7,302,355 B2 | 11/2007 | Jansen et al. |
| 7,314,048 B2 | 1/2008 | Couture et al. |
| 7,392,076 B2 | 6/2008 | Moctezuma de La Barrera |
| 7,400,246 B2 | 7/2008 | Breeding |
| 7,407,054 B2 | 8/2008 | Seiler et al. |
| 7,412,777 B2 | 8/2008 | Pelletier et al. |
| 7,419,492 B2 | 9/2008 | Yoon et al. |
| 7,427,272 B2 | 9/2008 | Richard et al. |
| 7,431,736 B2 | 10/2008 | Maroney et al. |
| 7,559,931 B2 | 7/2009 | Stone |
| 7,588,571 B2 | 9/2009 | Olsen |
| 7,594,933 B2 | 9/2009 | Kammerzell et al. |
| 7,634,306 B2 | 12/2009 | Sarin et al. |
| 7,657,298 B2 | 2/2010 | Moctezuma De la Barrera et al. |
| 7,668,584 B2 | 2/2010 | Jansen |
| 7,753,921 B2 | 7/2010 | Leitner |
| 7,780,681 B2 | 8/2010 | Sarin et al. |
| 7,840,256 B2 | 11/2010 | Lakin et al. |
| 7,876,942 B2 | 1/2011 | Gilboa |
| 7,877,131 B2 | 1/2011 | Jansen et al. |
| 7,885,705 B2 | 2/2011 | Murphy |
| 7,927,338 B2 | 4/2011 | Laffargue et al. |
| 7,970,190 B2 | 6/2011 | Steinle et al. |
| 7,995,280 B2 | 8/2011 | Kuss et al. |
| 8,000,926 B2 | 8/2011 | Roche et al. |
| 8,007,448 B2 | 8/2011 | Moctezuma de la Barrera |
| 3,034,057 A1 | 10/2011 | Penenberg |
| 8,057,482 B2 | 11/2011 | Stone et al. |
| 8,152,726 B2 | 4/2012 | Amoit et al. |
| 8,177,850 B2 | 5/2012 | Rudan et al. |
| 8,202,324 B2 | 6/2012 | Meulink et al. |
| 8,206,405 B2 | 6/2012 | Beverland et al. |
| 8,308,663 B2 | 11/2012 | Tuma |
| 8,400,312 B2 | 3/2013 | Hotokebuchi et al. |
| 8,425,557 B2 | 4/2013 | Kuiper et al. |
| 8,467,851 B2 | 6/2013 | Mire et al. |
| 8,482,606 B2 | 7/2013 | Razzaque et al. |
| 8,527,033 B1* | 9/2013 | Williams .............. A61M 5/427 600/424 |
| 8,554,307 B2 | 10/2013 | Razzaque et al. |
| 8,585,598 B2 | 11/2013 | Razzaque et al. |
| 8,641,621 B2 | 2/2014 | Razzaque et al. |
| 8,657,809 B2 | 2/2014 | Schoepp |
| 8,670,816 B2 | 3/2014 | Green et al. |
| 8,690,776 B2 | 4/2014 | Razzaque et al. |
| 2002/0069882 A1 | 6/2002 | Sklar |
| 2002/0077540 A1 | 6/2002 | Kienzle, III |
| 2002/0087101 A1 | 7/2002 | Barrick et al. |
| 2002/0198451 A1 | 12/2002 | Carson |
| 2003/0069591 A1 | 4/2003 | Carson et al. |
| 2003/0105470 A1 | 6/2003 | White |
| 2003/0153978 A1 | 8/2003 | Whiteside |
| 2003/0163142 A1 | 8/2003 | Paltieli et al. |
| 2003/0208296 A1 | 11/2003 | Brisson et al. |
| 2004/0068260 A1 | 4/2004 | Cossette et al. |
| 2004/0102792 A1 | 5/2004 | Sarin et al. |
| 2004/0106861 A1 | 6/2004 | Leitner |
| 2004/0143340 A1 | 7/2004 | Tuma et al. |
| 2004/0147926 A1 | 7/2004 | Iversen |
| 2004/0243148 A1 | 12/2004 | Wasielewski |
| 2005/0015002 A1 | 1/2005 | Dixon et al. |
| 2005/0021044 A1 | 1/2005 | Stone et al. |
| 2005/0049524 A1 | 3/2005 | Lefevre et al. |
| 2005/0065617 A1 | 3/2005 | Moctezuma de la Barrera et al. |
| 2005/0149050 A1 | 7/2005 | Stifter et al. |
| 2005/0197569 A1 | 9/2005 | McCombs |
| 2005/0245820 A1 | 11/2005 | Sarin |
| 2005/0251026 A1 | 11/2005 | Stone |
| 2005/0288609 A1 | 12/2005 | Warner et al. |
| 2006/0015119 A1 | 1/2006 | Plassky et al. |
| 2006/0084889 A1 | 4/2006 | Drumm et al. |
| 2006/0089657 A1 | 4/2006 | Broers et al. |
| 2006/0095047 A1 | 5/2006 | De La Barrera |
| 2006/0122516 A1 | 6/2006 | Schmidt et al. |
| 2006/0155382 A1 | 7/2006 | Katzman |
| 2006/0161052 A1 | 7/2006 | Colombet et al. |
| 2006/0189864 A1 | 8/2006 | Paradis et al. |
| 2006/0190011 A1 | 8/2006 | Ries |
| 2007/0106306 A1 | 5/2007 | Bodduluri et al. |
| 2007/0118139 A1 | 5/2007 | Cuellar et al. |
| 2007/0179568 A1 | 8/2007 | Nycz et al. |
| 2007/0225731 A1 | 9/2007 | Couture et al. |
| 2007/0239281 A1 | 10/2007 | Gotte et al. |
| 2007/0249967 A1 | 10/2007 | Buly et al. |
| 2007/0270686 A1 | 11/2007 | Ritter et al. |

(56) References Cited

U.S. PATENT DOCUMENTS

| | | |
|---|---|---|
| 2008/0027312 A1 | 1/2008 | Dick |
| 2008/0033442 A1 | 2/2008 | Amoit et al. |
| 2008/0051910 A1 | 2/2008 | Kammerzell et al. |
| 2008/0077004 A1 | 3/2008 | Henning |
| 2008/0125785 A1 | 5/2008 | Chana |
| 2008/0132783 A1 | 6/2008 | Revie et al. |
| 2008/0146969 A1 | 6/2008 | Kurtz et al. |
| 2008/0172055 A1 | 7/2008 | Mollard et al. |
| 2008/0183104 A1 | 7/2008 | Tuma et al. |
| 2008/0195109 A1 | 8/2008 | Hunter et al. |
| 2008/0214960 A1 | 9/2008 | Hodgson et al. |
| 2008/0228188 A1 | 9/2008 | Birkbeck et al. |
| 2008/0026959 A1 | 10/2008 | Revie et al. |
| 2008/0249394 A1 | 10/2008 | Giori et al. |
| 2008/0255584 A1 | 10/2008 | Beverland et al. |
| 2008/0269596 A1 | 10/2008 | Revie et al. |
| 2008/0269779 A1 | 10/2008 | Cadeddu et al. |
| 2008/0029425 A1 | 11/2008 | Revie et al. |
| 2008/0294265 A1 | 11/2008 | Warkentine et al. |
| 2008/0312529 A1 | 12/2008 | Amiot et al. |
| 2008/0319313 A1 | 12/2008 | Boivin et al. |
| 2009/0068620 A1 | 3/2009 | Knobel et al. |
| 2009/0087050 A1 | 4/2009 | Gandyra |
| 2009/0099570 A1 | 4/2009 | Paradis et al. |
| 2009/0105714 A1 | 4/2009 | Kozak |
| 2009/0125117 A1 | 5/2009 | Paradis et al. |
| 2009/0143670 A1 | 6/2009 | Daigneault et al. |
| 2009/0163930 A1 | 6/2009 | Aoude et al. |
| 2009/0209343 A1 | 8/2009 | Foxlin et al. |
| 2009/0248044 A1 | 10/2009 | Amiot et al. |
| 2009/0281545 A1 | 11/2009 | Stubbs |
| 2009/0289806 A1 | 11/2009 | Thornberry |
| 2009/0306499 A1 | 12/2009 | Van Vorhis et al. |
| 2009/0314925 A1 | 12/2009 | Van Vorhis et al. |
| 2009/0316967 A1 | 12/2009 | Dardenne et al. |
| 2009/0318931 A1 | 12/2009 | Stone et al. |
| 2010/0016705 A1 | 1/2010 | Stone |
| 2010/0063509 A1 | 3/2010 | Borja et al. |
| 2010/0069911 A1 | 3/2010 | Borja et al. |
| 2010/0076505 A1 | 3/2010 | Borja |
| 2010/0100011 A1 | 4/2010 | Roche |
| 2010/0137869 A1 | 6/2010 | Borja et al. |
| 2010/0153081 A1 | 6/2010 | Bellettre et al. |
| 2010/0192961 A1 | 8/2010 | Amiot et al. |
| 2010/0261998 A1 | 10/2010 | Stiehl et al. |
| 2010/0268067 A1 | 10/2010 | Razzaque et al. |
| 2010/0268249 A1 | 10/2010 | Stuart |
| 2010/0299101 A1 | 11/2010 | Shimada et al. |
| 2010/0312247 A1 | 12/2010 | Tuma |
| 2011/0092858 A1 | 4/2011 | Burger et al. |
| 2011/0160572 A1 | 6/2011 | McIntosh et al. |
| 2011/0190637 A1 | 8/2011 | Knobel et al. |
| 2011/0208093 A1 | 8/2011 | Gross et al. |
| 2011/0213379 A1 | 9/2011 | Blau et al. |
| 2011/0257653 A1 | 10/2011 | Hughes et al. |
| 2011/0264009 A1 | 10/2011 | Walter et al. |
| 2011/0320153 A1 | 12/2011 | Lightcap et al. |
| 2012/0022406 A1 | 1/2012 | Hladio et al. |
| 2012/0029389 A1 | 2/2012 | Amiot |
| 2012/0053594 A1 | 3/2012 | Pelletier et al. |
| 2012/0065926 A1 | 3/2012 | Lee et al. |
| 2012/0089013 A1 | 4/2012 | Whitmore |
| 2012/0143084 A1 | 6/2012 | Shoham |
| 2012/0157887 A1 | 6/2012 | Fanson et al. |
| 2012/0209117 A1 | 8/2012 | Mozes et al. |
| 2012/0232802 A1 | 9/2012 | Haimerl et al. |
| 2012/0247489 A1 | 10/2012 | Orban, III et al. |
| 2012/0283599 A1 | 11/2012 | Borja |
| 2012/0323247 A1 | 12/2012 | Bettenga |
| 2012/0330367 A1 | 12/2012 | Roche et al. |
| 2013/0030250 A1 | 1/2013 | Findeisen et al. |
| 2013/0096573 A1 | 4/2013 | Kang et al. |
| 2013/0116574 A1 | 5/2013 | Knobel et al. |
| 2014/0031722 A1 | 1/2014 | Li et al. |
| 2014/0031829 A1 | 1/2014 | Paradis et al. |
| 2014/0052149 A1 | 2/2014 | Van Der et al. |
| 2014/0094694 A1 | 4/2014 | de la Barrera |
| 2014/0107471 A1 | 4/2014 | Haider |
| 2014/0261453 A1 | 9/2014 | Carlson |
| 2014/0261456 A1 | 9/2014 | Malackowski et al. |
| 2014/0275940 A1 | 9/2014 | Hladio et al. |
| 2017/0069073 A1 | 3/2017 | Sela et al. |
| 2019/0290378 A1 | 9/2019 | Schwägli et al. |
| 2021/0038276 A1 | 2/2021 | Schwägli et al. |

FOREIGN PATENT DOCUMENTS

| | | |
|---|---|---|
| CN | 102711653 A | 10/2012 |
| EP | 1402839 A1 | 3/2004 |
| EP | 1563810 A1 | 9/2005 |
| FR | 2684287 A1 | 3/1991 |
| WO | 9732534 | 9/1997 |
| WO | 2004075768 A2 | 9/2004 |
| WO | 2004075768 A3 | 9/2004 |
| WO | 2006109983 A1 | 10/2006 |
| WO | 2006128301 A1 | 12/2006 |
| WO | 2007084893 | 7/2007 |
| WO | 2007095248 A2 | 8/2007 |
| WO | 2008151446 | 12/2008 |
| WO | 2009062314 | 5/2009 |
| WO | 2009117833 | 10/2009 |
| WO | 2010030809 A1 | 3/2010 |
| WO | 2010063117 | 6/2010 |
| WO | 2012080840 | 6/2012 |
| WO | 2013152436 A1 | 10/2013 |
| WO | 2013164770 A2 | 11/2013 |
| WO | 2013188960 A1 | 12/2013 |
| WO | 2014057352 A1 | 4/2014 |
| WO | 2014144321 A1 | 9/2014 |

OTHER PUBLICATIONS

Office Action for Corresponding Chinese Patent Application No. 201910642969.1; dated Nov. 1, 2021; 4 Pages; Chinese Translation.

Birrell et al, "Projecting the need for hip replacement over the next three decades: influence of changing demography and threshold for surgery," Annals of the Rheumatic Diseases, vol. 58, pp. 569-572 (1999).

Digioia III et al, "Comparison of a Mechanical Acetabular Alignment Guide With Computer Placement of the Socket," The Journal of Arthroplasty, vol. 17, No. 3, pp. 359-363 (2002).

Written Opinion dated May 22, 2012, relating to PCT International Patent Application No. PCT/IB2011/003246 issued from the Canadian Intellectual Property Office.

International Search Report for International Application No. PCT/IB2011/003246 dated May 22, 2012.

Int'l Preliminary Report on Patentability dated Jun. 7, 2011 in Int'l Application No. PCT/CA2009/001765; Written Opinion.

Int'l Search Report dated Feb. 18, 2010 in Int'l Application No. PCT/CA2009/001765.

Kanoh et al, "Accurate Acetabular Component Orientation After Total Hip Arthroplasty Using an Acetabular Alignment Guide," The Journal of Arthroplasty, vol. 00, No. 0, pp. 1-6 (2009).

Nogler et al, "Reduced variability in cup positioning: the direct anterior surgical approach using navigation," Acta Orthopaedica, vol. 79, No. 6, pp. 789-793 (2008).

PCT International Search Report dated Jul. 22, 2013 issued from the Canadian Intellectual Property Office relating to PCT International Application No. PCT/CA2013/000351.

PCT Written Opinion dated Jul. 22, 2013 issued from the Canadian Intellectual Property Office relating to PCT International Application No. PCT/CA2013/000351.

Seidel et al, "Hip joint center location from palpable bony landmarks—a cadaver study," Journal of Biomechanics, vol. 28, No. 8, pp. 995-998 (1995).

Solomon et al, "Surgical Anatomy for Pelvic External Fixation," Clinical Anatomy, vol. 21, pp. 674-682 (2008).

PCT International Search Report dated Jun. 17, 2014 issued from the Canadian Intellectual Property Office relating to PCT International Application No. PCT/CA2014/000241.

(56) References Cited

OTHER PUBLICATIONS

PCT Written Opinion dated Jun. 17, 2014 from the Canadian Intellectual Property Office relating to PCT International Application No. PCT/CA2014/000241.
Stryker Corporation; Orthomap Versatile Hip Navigation Manual; p. 10; 2012; USA.
Extended European Search Report dated Oct. 18, 2016 issued by the European Patent Office for corresponding European Patent Application No. EP 14765231.7 filed Jan. 7, 2016.
2nd Office Action dated Mar. 23, 2018 for corresponding Chinese Patent Application No. 2014800280161; 8 pages.
3rd Office Action dated Sep. 14, 2018 for corresponding Chinese Patent Application No. 2014800280161; 10 pages.
Search Report dated Apr. 24, 2019 For Corresponding Chinese Patent Application No. 2014800280161; 2 Pages.
Digioia III et al, "Surgical Navigation for Total Hip Replacement With the Use of HIPNAV," Operative Techniques in Orthopaedics, vol. 10, No. 1, pp. 3-8 (2000).
DiGioia, Anthony M., et al., "Comparison of a Mechanical Acetabular Alignment Guide with Computer Placement of the Socket", The Journal of Arthroplasty, vol. 17, No. 3, 2002, p. 359-360.
DiGioia, Anthony M., et al., "Surgical Navigation for Total Hip Replacement with the Use of Hipnav", Operative Techniques in Orthopaedics, vol. 10, No. 1, Jan. 2000, p. 3-8.
Int'l Preliminary Report on Patentability dated Jun. 7, 2011 in Int'l Application No. PCT/CA2009/007165; Written Opinion.
Toshiya Kanoh, MD, et al., "Accurate Acetabular Component Orientation After Total Hip Arthroplasty Using an Acetabular Alignment Guide", The Journal of Arthroplasty, vol. 25, No. 1, 2010, p. 81-85.
Written Opinion of the International Search Authority dated Feb. 18, 2010, relating to PCT International Patent Application No. PCT/CA2009/001765 issued from the Canadian Intellectual Property Office.

\* cited by examiner

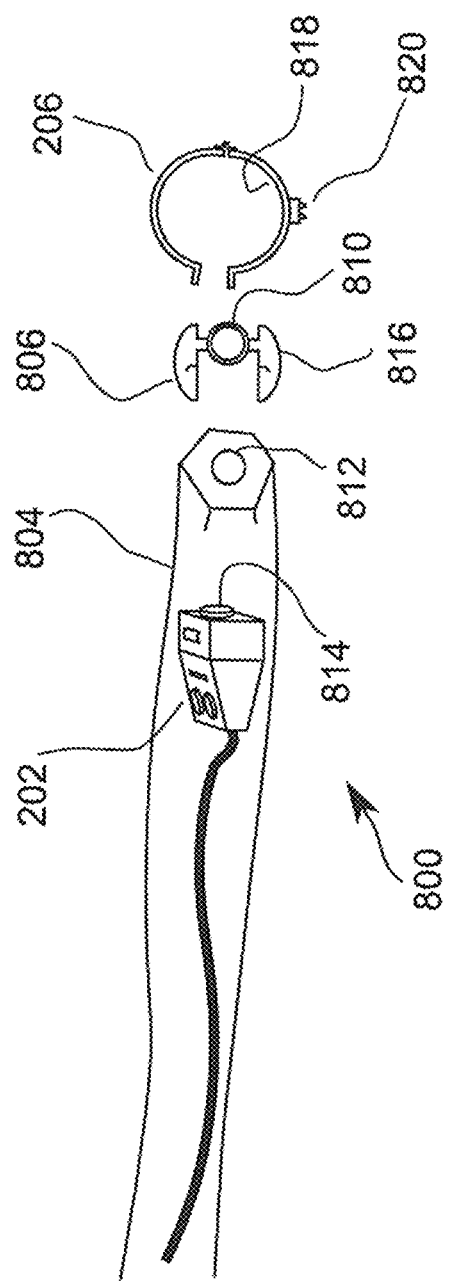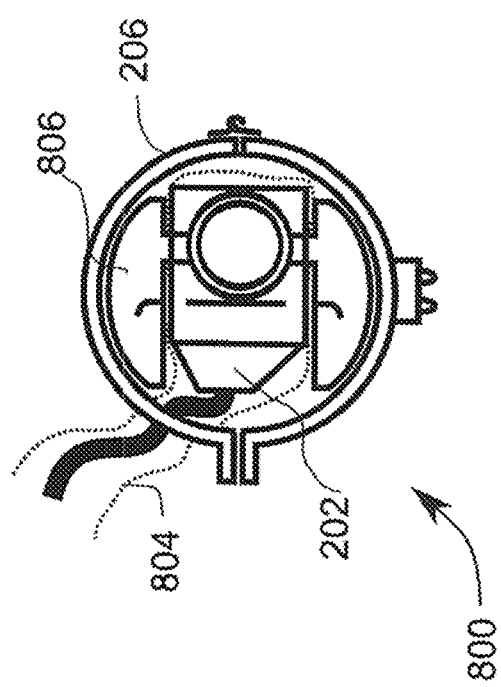
Figure 8A
Figure 8B

SYSTEMS AND METHODS TO COMPUTE A SUBLUXATION BETWEEN TWO BONES

CROSS REFERENCE

The present application is a continuation of U.S. Ser. No. 17/115,684 filed Dec. 8, 2020 and entitled "Systems And Methods To Compute A Subluxation Between Two Bones", the contents of which are herein incorporated by reference. U.S. Ser. No. 16/242,509 is a continuation of U.S. Ser. No. 16/242,509 filed Jan. 8, 2019 and entitled "Systems And Methods To Compute A Subluxation Between Two Bones", the contents of which are herein incorporated by reference. U.S. Ser. No. 16/242,509 is a continuation of U.S. Ser. No. 15/497,721 filed Apr. 26, 2017 and entitled "Systems and Methods to Compute a Positional Change Between Two Bones", (now U.S. Pat. No. 10,194,996) the contents of which are herein incorporated by reference. U.S. Ser. No. 15/497,721 is a continuation of U.S. Ser. No. 14/990,179 filed Jan. 7, 2016 and entitled "Sterile Optical Sensor System Having An Adjustment Mechanism" (now U.S. Pat. No. 9,655,749), the contents of which are herein incorporated by reference. U.S. Ser. No. 14/990,179 is a continuation of U.S. Ser. No. 13/833,181 filed Mar. 15, 2013 and entitled "System and Method for Intra-Operative Leg Measurement" (now U.S. Pat. No. 9,247,998), the contents of which are herein incorporated by reference.

TECHNICAL FIELD

The present disclosure relates generally to sterile surgical equipment. In particular the present disclosure relates to sterile optical sensor system having an adjustment mechanism to permit orientation of the sensor to view a surgical site.

BACKGROUND

In many surgical procedures, including joint replacement such as Total Hip Arthroplasty (THA), achieving precise positioning of tools and implants with respect to a patient's anatomy is critical for successful outcomes. FIG. 1 illustrates a pre-operative 100 and post operative 102 hip joint, along with a coordinate frame defining various directions 104. The post-operative hip joint is composed of a femoral component 106 and an acetabular component 108. In one THA technique, the hip joint is exposed and dislocated. The acetabulum and the femur are prepared for receiving implants. Typically, a cup prosthesis is to be implanted in acetabulum requiring alignment of the cup with respect to the patient's anatomy. Trial femoral prosthetics—available in various sizes to facilitate intra-operative adjustment—may be implanted to assess the correct final femoral implant size. The fit and sizing of the joint may be iteratively assessed and a final prosthetic hip joint (106 and 108) implanted.

Positioning prosthetic implants relative to the patient's anatomy may involve numerous challenges such as, selecting the correct implant geometry and altering the patient's bony anatomy (e.g. reaming, osteotomy, etc.), among others. Some important goals for a successful THA include: proper alignment of the acetabular cup; restoration or correction of leg length and offset; restoration of hip center-of-rotation (COR); and stability of new hip joint. The concept of leg length and offset change seems simple at first; however, it is a complex clinical and geometrical problem. The surgeon is often required to make various accurate assessments of leg length and offset intra-operatively.

BRIEF DESCRIPTION OF THE DRAWINGS

For a better understanding of embodiments of the systems, methods and devices described herein, and to show more clearly how they may be carried into effect, reference will be made, by way of example, to the accompanying drawings in which:

FIG. 8A is an exploded view of a pelvic clamp assembly in accordance with and example with a sterile drape with integrated optical window;

FIG. 8B is an end view of the pelvic clamp of FIG. 8A shown assembled with the sterile drape and a sensor;

It will be appreciated that for simplicity and clarity of illustration, elements shown in the figures have not necessarily been drawn to scale. For example, the dimensions of some of the elements may be exaggerated relative to other elements for clarity.

DETAILED DESCRIPTION

Figure 1:
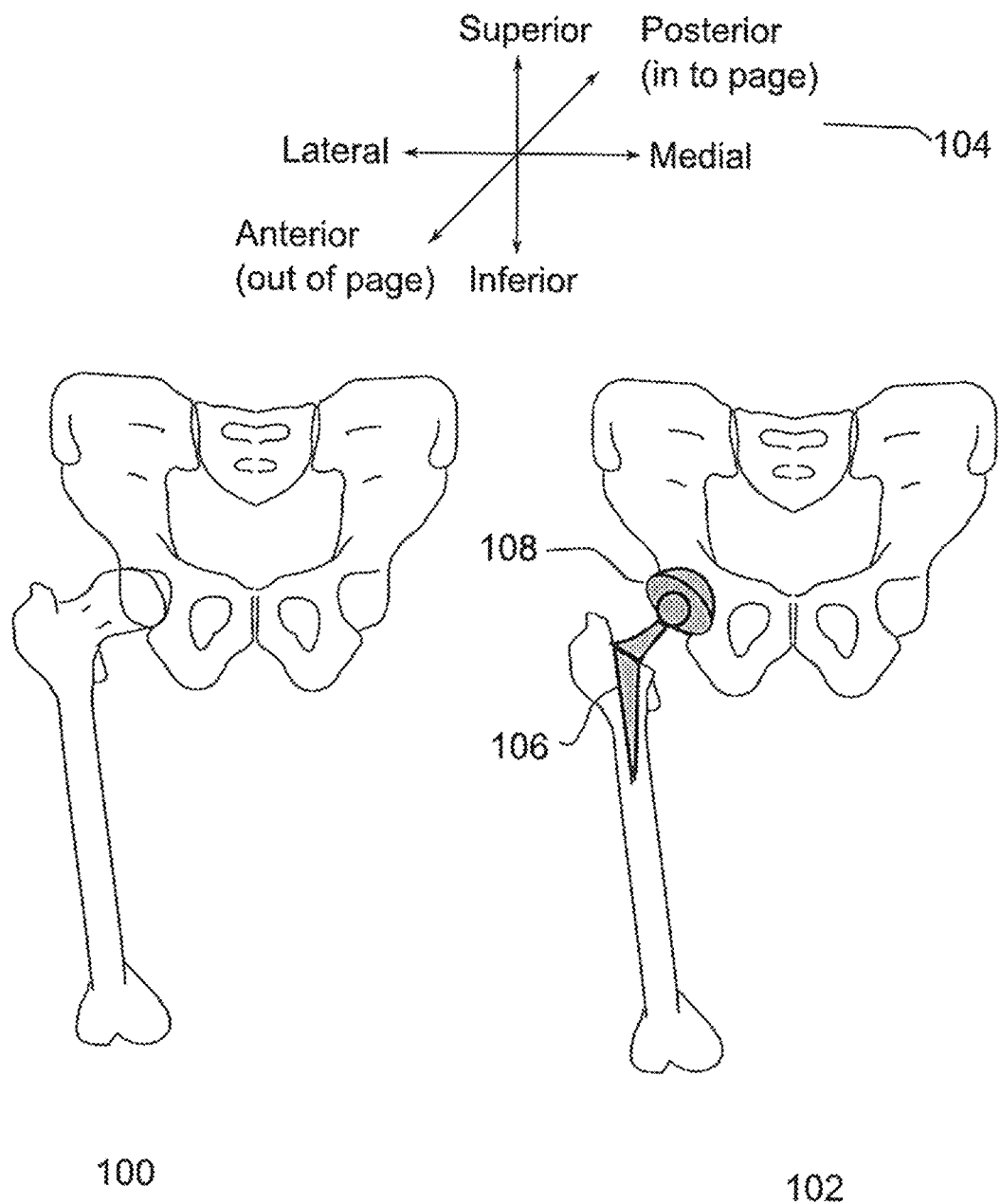
FIG. 1 is an illustration of a hip before and after THA including anatomical references frames in accordance with the prior art.

Pertaining to leg length and offset, with reference to FIG. 1, leg length change is defined as the change in femur position in the superior-inferior direction (i.e., if the femur translates in the inferior direction as a result of surgery, a positive leg length change has occurred). A leg length change may occur due to acetabular component placement, femoral component placement or sizing, or a combination of both. Note that in this figure, the femur and pelvis are aligned such that they have zero relative flexion, rotation and abduction. This relationship is said to be "neutral". If the femur was not neutral with respect to the pelvis, then the coordinate frame of the femur would not align with the pelvis, but rather be rotated by the same amount as the femur; for example, if the femur were abducted by 90 degrees, then the femur's inferior direction would be the pelvis' lateral direction. In this case, it is clear that the total leg length change is the leg length change due to the acetabular component position (in the pelvis coordinate frame) summed with the leg length change due to the femoral component position (in the femur coordinate frame). It is also clear that, when neutral, both frames align, simplifying the problem.

Offset change is analogous to leg length change; however, it is in the lateral-medial direction (i.e. if the femur translates laterally as a result of the surgery, then a positive offset change has occurred). Occasionally in the art of hip arthroplasty, offset is not defined purely in the medial-lateral direction (in the patient's coronal plane), but rather in a plane rotated about the patient's mid-line by the amount of femoral version (typically 10-15 degrees). The femoral prosthetic does not sit purely in the medial-lateral plane; it is rotated (with reference to FIG. 1) slightly forward, such that the ball sits more anteriorly than the stem. This alternative definition of offset would be as if the femur were internally rotated (by approximately 10-15 degrees) such that the femoral prosthetic was purely in the coronal plane.

Some technical terms and definitions will be useful throughout this document. The art of tracking is chiefly concerned with positions and orientations. The terms "coordinate system", "coordinate frame", "reference frame", etc, refer to a standard basis in which positions and orientation may be described. The terms "pose" (position and orientation state estimate), position, relative position, spatial positioning, etc, all refer to describing the position and/or orientation of a rigid body with respect to some coordinate frame.

There are provided systems, methods and computer program products for navigational guidance systems. In one example, intra-operative leg position measurements are provided during hip arthroplasty. Provided is an optical sensor for coupling to a pelvis and a target for coupling to a femur in alignment with the sensor. The sensor provides positional signals to a processing unit for determining a relative position of the sensor and target. The processing unit is configured to use a baseline measurement of leg position and a map to calculate and display leg position measurements in real time. The map is defined through a registration range-of-motion (RROM) procedure where instructions are presented for moving the femur in at least two planes to generate signals to calculate the map. Leg position may be leg length and/or offset and/or anterior-posterior position of the leg. The map is used to present the leg position measurements in an anatomical, rather than a sensor, coordinate frame.

There is disclosed a system for providing intra-operative leg position measurements during hip arthroplasty of a pelvis and a femur at a surgical site. The system comprises: an optical sensor for coupling to the pelvis and for alignment with the surgical site; a target for coupling to the femur in alignment with the sensor, the sensor providing signals in response to the target for determining relative positions of the sensor and target; and a processing unit for communicating with the sensor, the processing unit configured to use a baseline measurement of leg position and a map to calculate and display leg position measurements in real time, where the map is defined through a registration range-of-motion (RROM) procedure. The processing unit may receive first signals from the sensor and determines the relative position of the sensor and target to determine the baseline measurement, a plurality of second signals generated through the RROM to define the map and a plurality of third signals to display leg position measurements in real time using the baseline measurements and the map. The processing unit may present instructions, via a graphical user interface, for moving the femur in at least two planes to generate the plurality of second signals during the RROM procedure. In one example, the leg position is leg length and offset. The processing unit may use the map to present the leg position measurements in an anatomical coordinate frame. The leg position measurements can be displayed independently of an orientation of the femur. In one example, the processing unit is further configured to detect hip joint subluxation in real time and alert in accordance with the detection.

There is disclosed a method for performing a hip arthroplasty with intra-operative digital leg position guidance comprising: determining and storing a pre-dislocation baseline femur position by a processing unit using a sensor and a target providing signals for determining a relative position; performing a registration range of motion (RROM) procedure, after a prosthetic joint reduction, by the processing unit to define a RROM map to an anatomical coordinate frame for leg position measurements generated using the signals; and displaying leg position measurements in real-time on a display using the baseline femur position and RROM map. The method may comprise receiving the signals by the processing unit in response to an intra-operative movement of the femur and calculating the leg position measurements for intra-operative display. In one example, the method may comprising detecting and alerting of hip joint subluxation by the processing unit in response to the leg position measurements. A computer program product aspect is also disclosed in which there is a computer program product for performing a hip arthroplasty with intra-operative digital leg position guidance comprising non-transitory medium storing instructions and data for configuring the execution of a processing unit to perform such as in accordance with the method.

There is disclosed a system to provide intra-operative guidance during a medical procedure comprising: a single sensor, for coupling to a bone and orienting toward a site for the medical procedure; a single target, coupled to an object, for tracking by the sensor; and, a processing unit for communicating with the sensor, the processing unit displaying a relative position of the object and the bone, in accordance with a relative position of the target and the sensor calculated using the positional signals from the sensor. The bone may be a pelvis. The object may be a femur. The processing unit can calculate a registration by prompting movement of the object while collecting pose data. The medical procedure may be a surgical procedure, for example, a hip arthroplasty procedure. In one example, the bone is a pelvis and the object is a femur and the processing unit calculates a leg length and offset change measurement intra-operatively.

There is disclosed a method to provide intra-operative guidance during a medical procedure comprising: receiving at a processing unit a plurality of positional signals from a single sensor coupled to a bone and oriented toward a site for the medical procedure, the positional signals generated for a single target, coupled to an object, for tracking by the sensor; calculating by the processing unit a relative position of the object and the bone in accordance with the positional signals; and intra-operatively displaying the relative position on a display. The bone may be a pelvis. The object may be a femur. The method may include calculating, by the processing unit, a registration by prompting movement of the object while collecting pose data. The medical procedure may be a surgical procedure, for example, a hip arthroplasty procedure. In one example, the bone is a pelvis and the object is a femur and the method further comprises calculating, by the processing unit, a leg length and offset change measurement intra-operatively.

There is disclosed a computer program product comprising a non-transitory medium storing instructions and data for configuring the execution of a processing unit to receive a plurality of positional signals from a single sensor coupled to a bone and oriented toward a site for the medical procedure, the positional signals generated for a single target, coupled to an object, for tracking by the sensor; calculate a relative position of the object and the bone in accordance with the positional signals; and intra-operatively display the relative position on a display.

There is disclosed a medical navigational guidance system comprising: a sensor for coupling to a bone and orienting toward a site for a medical procedure; a target, coupled to an object, for tracking by the sensor; and, a processing unit in communication with the sensor, the processing unit configured to guide alignment of the sensor with the target, the processing unit using positional signals from the sensor to calculate and display, using a user interface, directional instructions to move into alignment the sensor and target. The system may comprise an alignment mechanism facilitating two degrees of freedom orientation adjustment of the sensor with respect to the bone. The alignment mechanism may be a locking mechanism to releasably fix the orientation of the sensor. The alignment mechanism is a lockable ball joint. The target may be used to define the location of the site. The processing unit may represent the pivoting orientation of the sensor as a crosshair on a display screen and the location of the surgical site as a bull's eye target. The system may comprise a releasable coupling for coupling the sensor to the bone.

There is disclosed a method of performing a medical procedure under navigational guidance comprising guiding, using a processing unit and a display, the alignment of a sensor configured to track a target at a site for the procedure, the processing unit receiving positional signals from the sensor and calculating and displaying, using a user interface, directional instructions to move into alignment the sensor and target. The sensor may be coupled to a bone and is capable of pivoting orientation in at least two degrees of freedom not including pivoting about an optical axis of the sensor. The pivoting orientation is lockable to maintain alignment. The processing unit signals to lock the pivoting orientation in response to the alignment. The target may be used to define the site. The method may comprising displaying the pivoting orientation of the sensor in 2 degrees of freedom. The user interface may indicates the location of the surgical site in 2 degrees of freedom. In one example, the user interface represents pivoting orientation of the sensor as a crosshair on the display screen, and the location of the surgical site as a bull's eye target. The bone may be a pelvis. The target may be placed on a femur.

There is disclosed a computer program product comprising a non-transitory medium storing instructions and data for configuring the execution of a processing unit to perform guiding, using a display, the alignment of a sensor configured to track a target at a site for a medical procedure, the processing unit receiving positional signals from the sensor and calculating and displaying directional instructions to move into alignment the sensor and target.

There is disclosed a system for making sterile a non-sterile sensor for use in navigational guidance during surgery. The system comprises: a sterile drape having an optically transparent window for draping the sensor in a sterile barrier; a shroud, which when engaged with a draped optical sensor, secures the sensor through the drape in alignment with the window without breaching the sterile barrier; and a clamp, which, in its closed and position, is configured to rigidly hold the assembled shroud, drape and sensor, while preserving the optical sensor alignment in the window. The shroud and the clamp may have respective mating surfaces which, when the sensor is in the shroud and the clamp is in a partially closed position, enable relative movement of the shroud and clamp to adjust the orientation of the sensor. The respective mating surfaces may define portions of respective spheres. The clamp is configured for coupling to a bone, for example, using a releasable quick connect mechanism. A method aspect therefor is also disclosed.

A method and system for surgical tracking has been presented in Applicant's U.S. patent application Ser. No. 13/328,997 filed Dec. 16, 2011 and entitled "Method And System For Aligning A Prosthesis During Surgery", which application published as Publication No. 2012/0157887 dated Jun. 21, 2012, the content of which is incorporated herein in its entirety. This method and apparatus obviates the requirement for a stationary, fixed baseline stereo camera located outside the surgical field; instead, an optical sensor combined with a target are fixed directly to the patient's anatomy and surgical instruments within the surgical field. This architecture is well-suited to measure relative pose, since the sensor is directly coupled to one of the objects being tracked. It is also well-suited toward surgical applications, which typically have a relatively small surgical working volume. This method and apparatus for positional tracking can be applied to various surgical (and in particular, orthopaedic) procedures. In particular, it may be used during THA to provide intra-operative guidance to the surgeon for leg length and offset.

Figure 2:
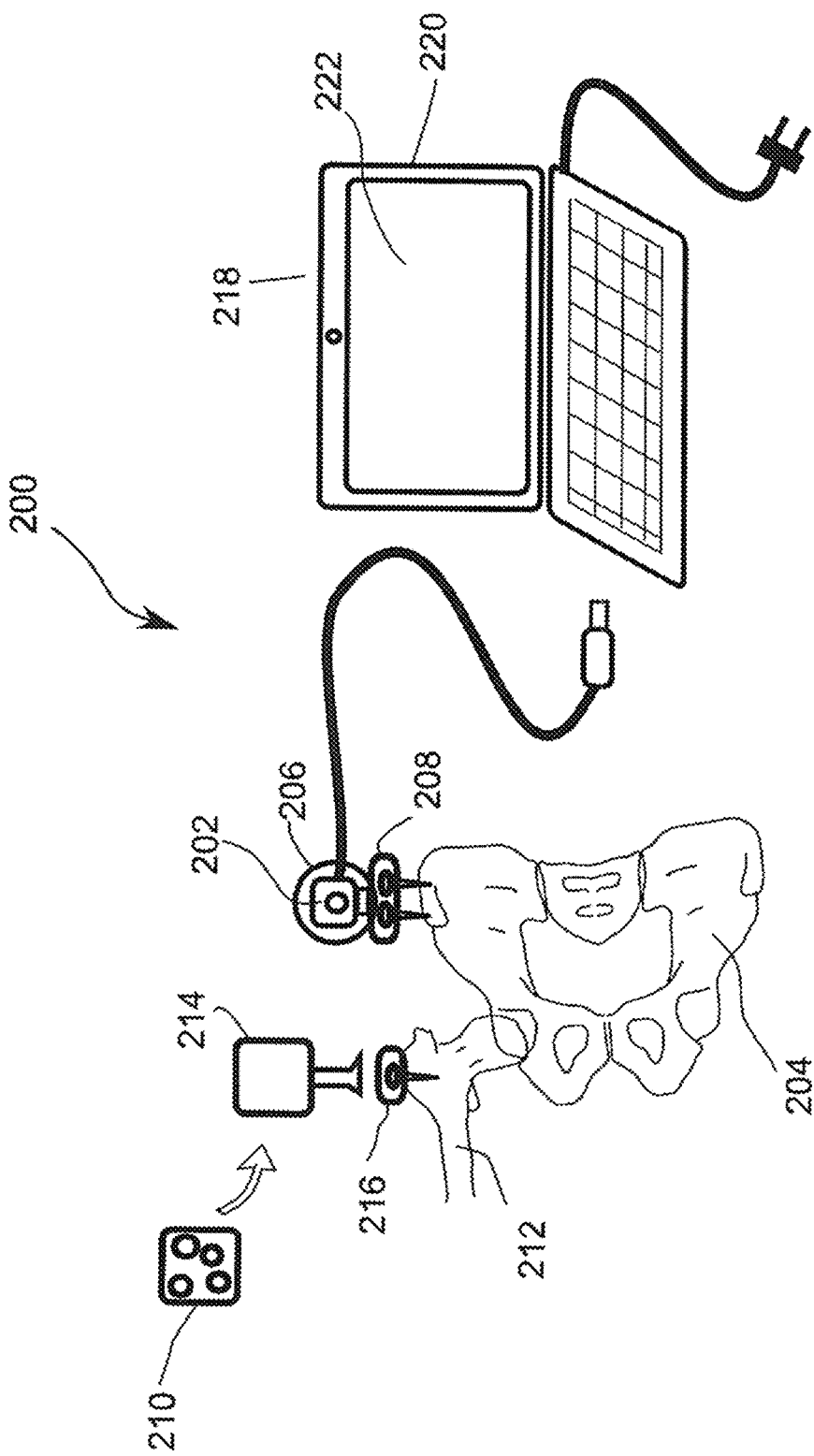
FIG. 2 is an example of a system for determining and presenting leg length and offset measurements intra-operatively.

With reference to FIG. 2 herein, one example system in which a sensor is directly coupled to one of the objects being tracked is a system 200, which provides intra-operative leg length and offset change measurements (e.g. determining relative positions, monitoring changes and presenting measurements) to a surgeon. In this system 200, a goal is to measure leg length and offset (from references on the pelvis and femur) in real-time. There is a sensor 202 coupled to the patient's pelvis 204 via a pelvic clamp 206 and a pelvic platform 208. The pelvic platform provides a mechanically rigid connection to the pelvis, for example, using bone pins or screws. The pelvic clamp has three functional characteristics: to attach the sensor to the pelvic platform; to provide a means to aim the sensor towards the surgical site (when attached to pelvic platform); and, to provide a repeatable quick-connection point between the pelvic platform and the pelvic clamp/sensor assembly (such that the surgeon may remove this assembly when not in use, or as a first point of failure in case of an unintended mechanical blow).

Again, in reference to FIG. 2, there is a target 210 coupled to the femur 212 via a beacon 214 and a femur platform 216. The femur platform provides a mechanically rigid connection to the femur, for example, using bone pins or screws. The beacon has two functional characteristics: to attach the target to the femur platform, and to provide a repeatable quick connection point between the femur platform and the beacon/target assembly (such that the surgeon may remove this assembly when not in use, or as a first point of failure in case of an unintended mechanical blow).

There is symmetry in this system's architecture on the pelvic and femoral sides. The following system components are analogous, in the sense that they fundamentally serve similar functions: pelvic and femur platforms are used for rigid connections to bone; pelvic clamp and beacon are used to interface to their respective platforms, provide a quick connection, and attach to the sensor/target; the sensor and target are the tracking system components, which are simultaneously used to measure their relative pose. Having such symmetry and structure in this device is advantageous. It simplifies mechanical design, manufacture and tolerance analysis (e.g. the same quick-connection mechanism may be used on both pelvic and femoral sides). It also provides modularity and flexibility (e.g. a different beacon design can be implemented without changing the femur platform or target designs), which is highly important when considering additional surgical applications (for example, knee arthroplasty).

Within the operation of the tracking system 200, the sensor 202 senses the target 210, and provides an output to a workstation 218 or other processing unit (e.g. by any means of communication, for example, USB) for processing by a processor or processors (not shown) such as may be configured by a computer program or programs 220 (e.g. one or more applications, operating systems, etc. or other software, instructions and/or data) stored to a computer medium (not shown), such as a non-transitory medium, for execution by the processor or processors in order to determine the pose between the target 210 and the sensor 202 (and hence, the pelvis and the femur). It will be appreciated that the description of the workstation is simplified. In another example embodiment, the methods are implemented primarily in hardware using, for example, hardware components such as application specific integrated circuits (ASICs). Implementation of the hardware state machine so as to perform the functions and methods described herein will be apparent to persons skilled in the relevant art(s). In yet another embodiment, the methods are implemented using a combination of both hardware and software.

In particular, the sensor 202 is optical, and the sensor output signals represent a 2-dimensional image. The target is visible to the optical sensor, and has an identifiable pattern. By processing the image output of the sensor, and with a priori knowledge of the target's pattern geometry, the workstation 218 is able to calculate relative pose. In addition to calculating relative pose, the workstation 218 may display information to a surgeon via a Graphical User Interface (GUI) in real-time such as presenting information via a display 222. Representative screen shots in accordance with an example are described herein below. This information may be displayed in any coordinate frame; however, it is preferable to display pose information to a surgeon in an anatomical coordinate frame. The software workflow preferably cooperates with the surgical workflow, and may: prompt the surgeon to perform certain actions, collect certain data, verify integrity of data, detect errors, display data at clinically appropriate times, log data, etc.

In the present example, the positional navigation system relies on one sensor and one target only, in order to provide intra-operative leg length/offset measurements. This is a reduction in complexity relative to existing computer navigation systems, which have fundamental requirements to: process multiple images (stereo camera) and track multiple objects simultaneously (pelvis, femur, stylus/other instruments).

Figure 3:
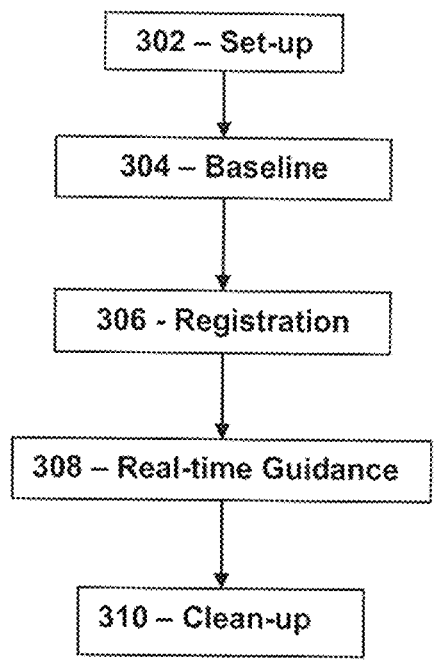
FIG. 3 is a process chart showing operations for use of leg length and offset measurement in accordance with an example.

FIG. 3 is a process chart that describes a method of using system 200 in order to intra-operatively measure and display changes in leg length and offset to a surgeon during THA. During "Set-up" 302, the system is prepared for use. This step 302 may occur while the surgical personnel are performing their standard surgical preparation, immediately prior to the operation. In step 302, the workstation 218 is set-up in an appropriate location and powered on. The sensor 202 is connected. Since this is a surgical device, the components of the system which are used within the sterile field are provided sterile (whether terminally sterile, protected with a sterile drape, or re-processed within the hospital). Also, in step 302, the beacon 214 and target 210 are assembled. At the conclusion of this step, the system 200 is ready for use.

The objective of the next step 304, called "Baseline", is to determine and store a pre-operative leg length and offset reference. This step 304 occurs preferably immediately prior to the dislocation of the native hip joint, after the hip is surgically exposed. The femur platform 216 and pelvic platform 208 are mounted to their respective bones, in order to provide rigid structures for the sensor 202 and target 210 of the system 200. The beacon 214 (coupled with the target 210) is preferably mounted onto the femur platform 216. The sensor 202 is then placed within the pelvic clamp 206. Initially, the sensor 202 may have its orientation within the pelvic clamp 206 adjusted. In order to align the sensor 202 with the surgical site, the software 220 (via a graphical user interface on display 222) may guide the surgeon to align the orientation of the sensor 202 based on the pose of the target 210 (mounted on the femur, which represents the position of the surgical site). Upon suitable alignment, the surgeon may lock the pelvic clamp 206 and sensor 202 in place, such that the orientation is no longer adjustable. At this time, the system 200 is prepared to determine and store a pre-operative leg length and offset reference.

The desired pre-operative leg length and offset reference is used as a basis to compute change in leg length and offset. This reference measurement is a pose, and may be triggered by the surgeon (e.g. by pressing a button located on the sensor 202). Note that the reference measurement (pose) is not expressed in anatomical coordinates (since no registration procedure has occurred yet), but rather in the sensor 202 coordinate frame. This reference baseline pose is stored by the software 220 for later use. The system 200 measures changes in leg length and offset; it is up to the surgeon and their pre-operative planning to determine their desired values of leg length and offset change (typically done by analyzing left and right hips using pre-op radiographs). Note that during baseline measurement, it may be necessary for the femur to be substantially "neutral" with respect to the pelvis; this means that the femur coordinate frame is aligned with the pelvic coordinate frame, or in clinical terms, that the femur has zero flexion, zero adduction and zero rotation (it is possible to alleviate this requirement where a femur registration is explicitly performed, and when the pre and post operative COR are known).

After a baseline measurement of leg length and offset is recorded, the surgeon may proceed with the hip arthroplasty. The beacon 214 (with target 210) and pelvic clamp 206 (with sensor 202) may be removed using their respective quick connections, so as not to clutter the surgical site (leaving the low-profile pelvic platform 208 and femur platform 216 in place).

Typically, surgeons perform a first trial reduction using a final acetabular shell with trial components (e.g. liner, broach neck, head). It is at this time when the function of the prosthetic hip joint is assessed, including assessing the resulting change in leg length and offset. Normally surgeons unequipped with computer navigation assess the change in leg length and offset using ad hoc techniques.

In order for the system 200 to provide meaningful real-time measurements of leg length and offset to the surgeon, a registration must occur. Registration refers to a process in which the map between the tracking system's coordinate frame (i.e. the sensor 202) and the patient's anatomical coordinate frame is determined. It is known to perform registration when using known fixed stereo camera-based positional navigation systems. Such registration is normally accomplished with a tracked "probe" or "stylus", which contacts anatomical landmarks, and reconstructs the patient's anatomical coordinate frame in this manner. The systems (e.g. 200) and methods described herein can accommodate "probe" or "stylus" based registration; however, operation without use of a probe or stylus may be preferred.

In reference to step 306 ("Registration") a registration procedure involving moving the femur in pre-defined and known motions (with the sensor 202 and target 210 attached in their respective anatomical locations) is used to map the patient's anatomy. This procedure will be referred to as the Registration Range-of-Motion (RROM). The RROM procedure may be advantageous for the following reasons:

- it obviates the need for an additional system component for registration (e.g. tracked stylus);
- the surgeon typically performs a clinical range-of-motion test contemporaneously (i.e. this method of registration matches the existing surgical workflow);
- the pre-defined motions are well-known in clinical terminology and practice;
- the RROM data is also used to calculate the hip COR (no additional data necessary)

In particular, the RROM procedure may prompt the surgeon to move the femur in flexion/extension, internal/external rotation, and/or abduction/adduction, while the sensor 202 (coupled to the pelvis), in conjunction with the software 220, tracks the pose of the target 210 (coupled to the femur). For example, the GUI on display 222 may prompt the surgeon to move the femur in the flexion-extension direction; since this motion lies in a plane, the pose tracking data may be further processed by the software 220 in order to determine the equation of the plane in the sensor's 202 coordinate frame. In order to determine the patient's principal anatomical reference frame (and hence, resolve measurements into leg length and offset coordinates), it is preferred to collect tracking system pose data of at least two planes (since an orthogonal reference frame can be determined from two planes). An example of the workstation 218 (e.g. software) prompting the surgeon during the RROM procedure is found in the GUI of FIG. 4. Here, the surgeon is prompted to move the leg in pre-defined motions, as shown in the instructional graphic 402 (note that the instructional graphic does not necessarily show the patient's anatomy, but rather a generic representation of a pelvis and a femur and portions of system 200 that is intended to be instructional). The motions are described in clinical terms 404. During the execution of the motions, the workstation 218 accumulates pose data until a sufficient amount is collected, as indicated by the progress bars 406. The amount of pose data is deemed sufficient when there is a high confidence that the pose data associated with each motion will yield an accurate anatomical feature (i.e. plane); for example, in order to mitigate random noise and outliers, a minimum number of pose data points, including a minimum variance in pose, may be required.

Figure 4:
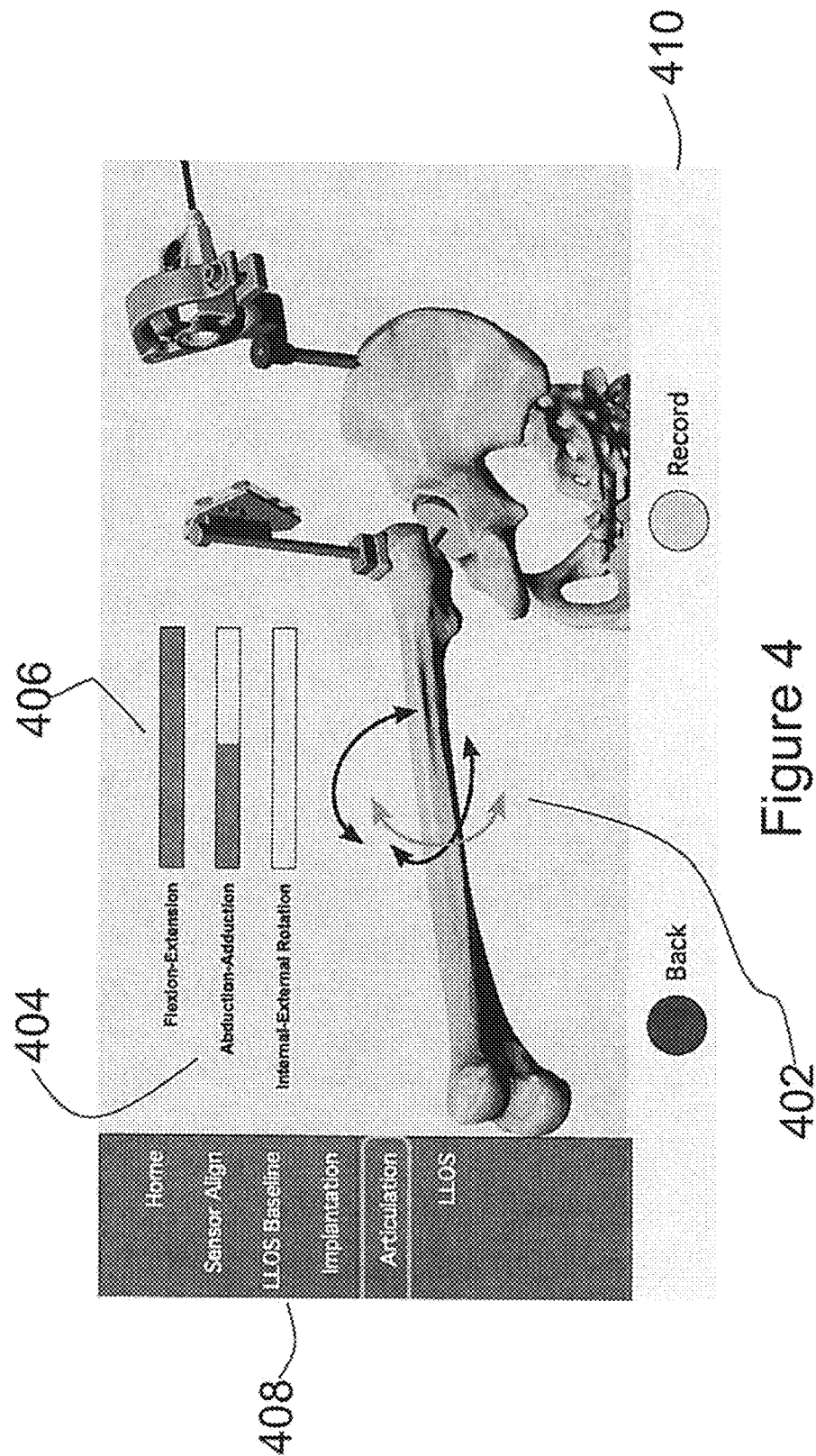
FIGS. 4 and 5 are screen shots of a representative graphical user interface showing leg length and offset registration and measurements in accordance with an example.

In further reference to the GUI of FIG. 4, a navigation panel 408 is shown, which is intended to provide a surgeon with an indication of their current step in the process. Also, further instructional indicators 410 are shown. The indicators 410 correspond to user inputs (for example, buttons on sensor 202) which the surgeon interacts with, and the labels provide instruction on the action resulting from each user input. For example, in this case, one user input might cause the system 200 to go back to the previous step (as indicated in the navigation panel 408), whereas another user input might trigger an action in accordance with the current step in the process (e.g. trigger the collection of RROM pose data). The navigation panel 408 and instructional indicator 410 may persist throughout the various stages and GUI's of the software 220.

The RROM procedure 306 occurs after the trial reduction, meaning that the acetabular cup or shell has already been implanted. Not only is this advantageous since it matches the existing surgical workflow, but the prosthetic joint will facilitate a smooth motion, whereas a native hip joint might not (e.g., due to flexion contractures, bony impingement, arthritic deformities, etc).

Figure 5:
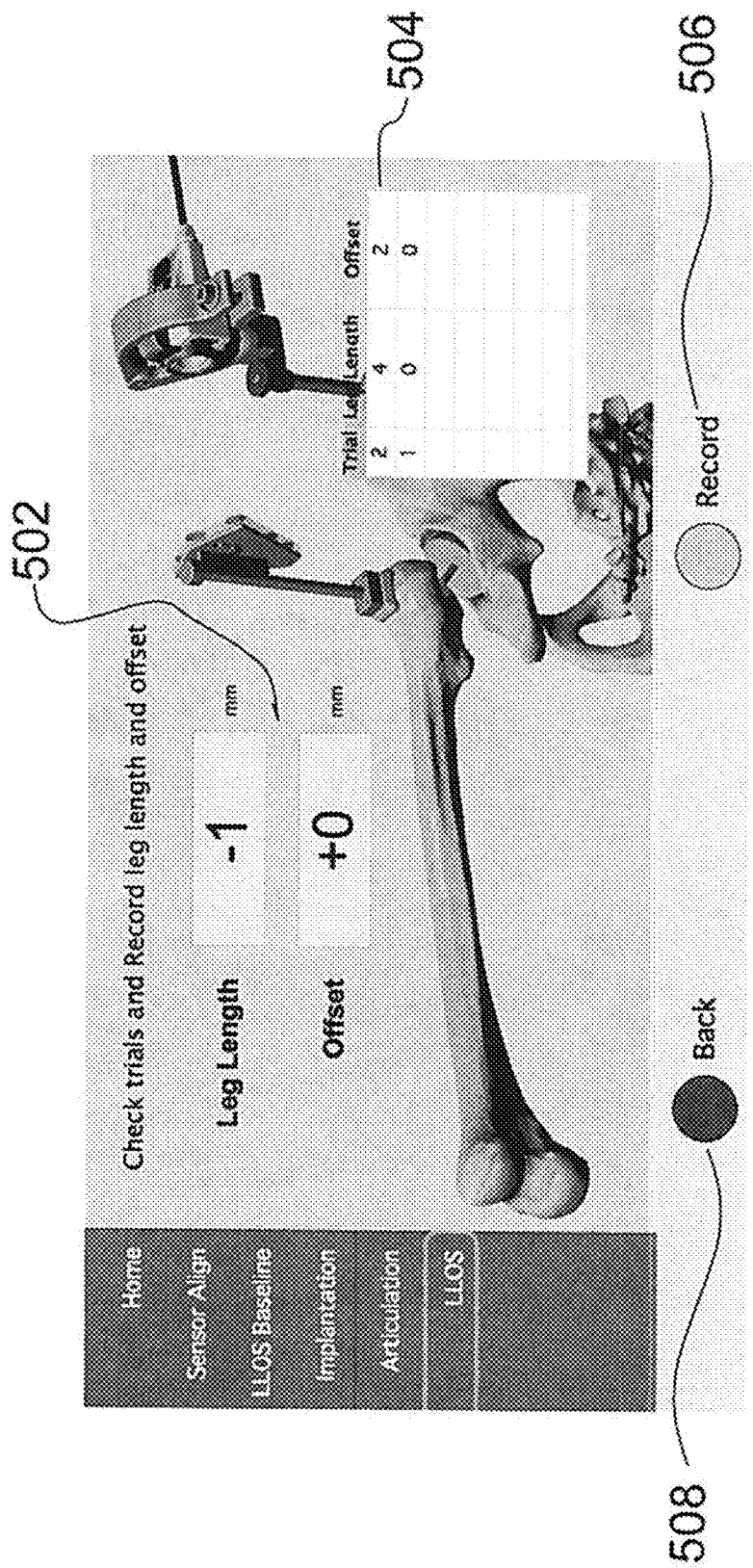

At the conclusion of the RROM procedure, the software has calculated a map from the patient's coordinate frame to the sensor 202, as well as the position of the hip COR (with respect to the sensor 202). Both pieces of information are useful for the "Real-time Guidance" step 308. In this step, real-time measurements of leg length and offset are provided to the surgeon via the GUI on the display 222. For example, FIG. 5 shows a graphical user interface including a display of leg length and offset change 502 (updating in real-time), as well as snapshots of leg length and offset changes 504, which may be captured at the surgeon's discretion (for example, to aid in keeping track of numbers amongst several joint reductions), for example, by pressing the "record" button on the sensor 202. The surgeon may use the real-time leg length and offset information to select trial and final implant sizes to meet their desired pre-operatively planned leg length and offset changes. Note that the transition from the GUI of FIG. 4 to the GUI of FIG. 5 may be configured to occur automatically, at the conclusion of the Registration step 306.

During the "Real-time Guidance" step 308, measurements of leg length and offset change are not influenced by the femur's orientation. This is significant, because other existing products are very sensitive to returning the femur to the original baseline orientation in order to maintain accuracy. In this system and method, the RROM calculates the patient's anatomical coordinate frame and hip COR, which facilitates a "virtual" realignment of the femur, however it is oriented, with the baseline measurement orientation. In simple terms, this system and method automatically compares "apples to apples" when calculating leg length and offset change.

In the "Clean up" step 310, the device is removed from the patient, single-use components are discarded, other components are powered down, cleaned, stowed, etc. This step occurs after the surgeon is satisfied with the leg length and offset change effected, and/or after the final prosthetic hip joint has been implanted.

Figure 6:
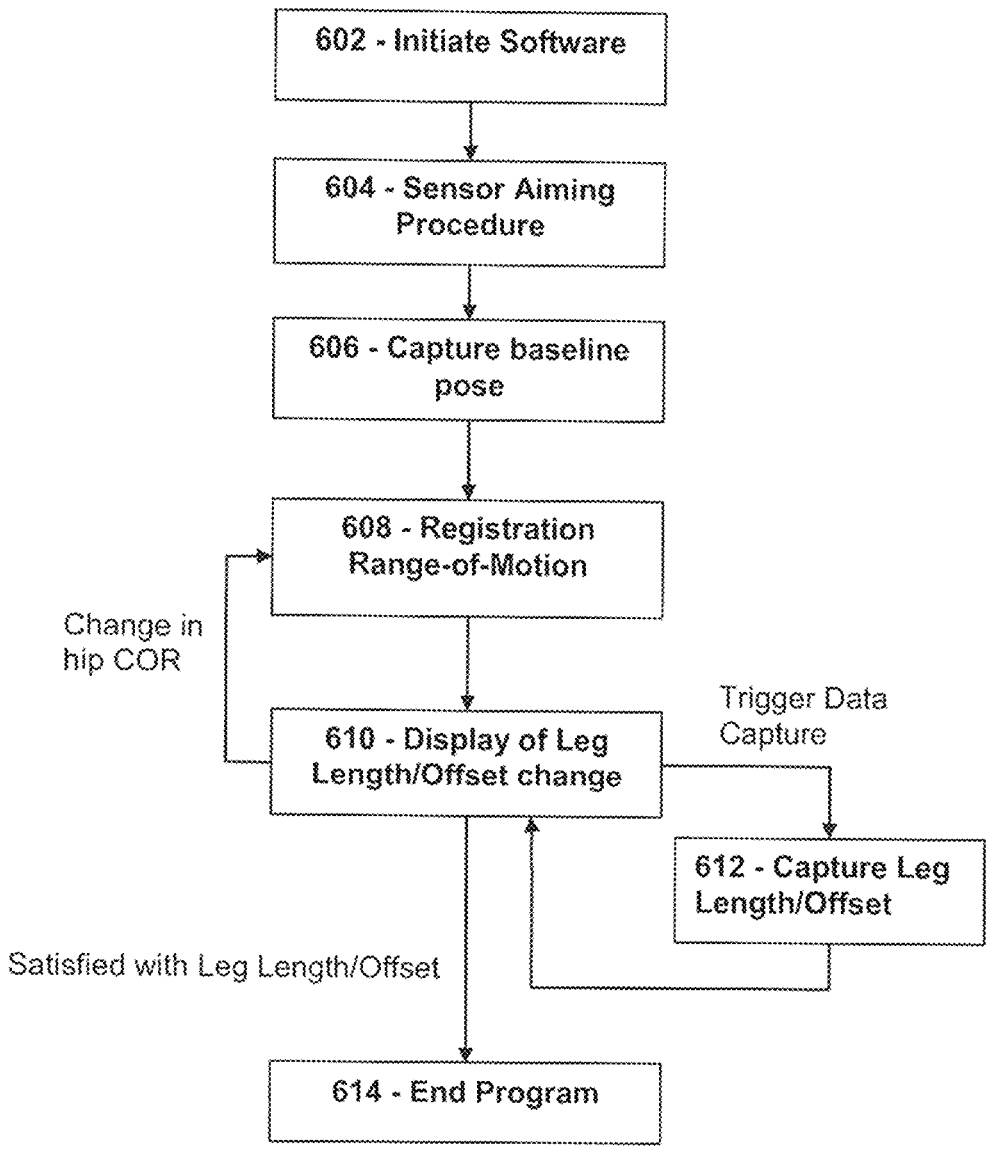
FIG. 6 is a flow chart of operations of a workstation or other processing unit to provide leg length and offset measurement in accordance with an example.

FIG. 6 is a flow chart of operations of workstation 218 to provide leg length and offset measurement in accordance with an example. The software, which is a part of system 200, executes on the workstation and provides functions and work flow that cooperate with the clinical workflow, as outlined in FIG. 3. In step 602, the software is initialized and made ready for use. For example, the surgeon or another user may select an operative hip (right or left), as well as ensure that the sensor 200 is plugged in and operational. The surgeon may then advance the software.

Figure 7:
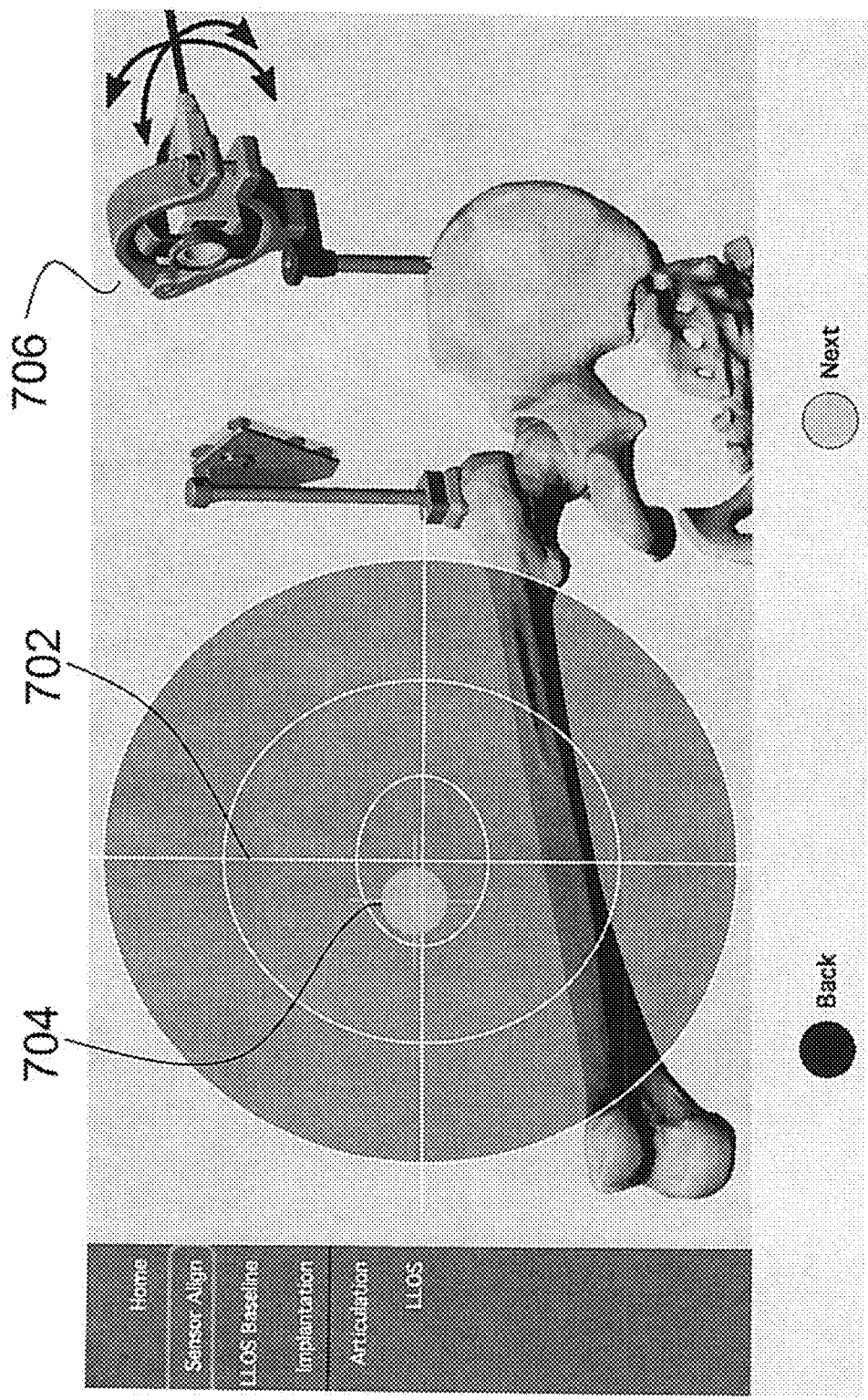
FIG. 7 is a screen shot of a representative graphical user interface showing sensor and target alignment in accordance with an example.

After the initial incision and installation of the femur platform 216, beacon 214, target 210, pelvic platform 208 and pelvic clamp 206, the sensor 202 may be aligned and secured. In step 604, the software 220 guides the surgeon in aligning (and securing) the sensor 202 such that it is aimed at the surgical site. This may be accomplished via a GUI, as shown in FIG. 7. This GUI uses a "bull's eye" graphic 702 and real-time alignment indicator 704, shown as crosshairs, such that the surgeon is prompted to hit the "bull's eye" 702 with the crosshairs 704, by adjusting the angle of sensor 202, as indicated by the instructional graphic 706. The angle of the sensor 202 is preferably adjustable in at least two rotational degrees of freedom which facilitate its alignment toward the surgical site (i.e. rotating the sensor 202 about its optical axis will not help; the other two rotational degrees of freedom are required to align the sensor 202 with the surgical site). The basis for alignment may be the pose of the target 210, coupled to the patient's femur, as shown in the instructional graphic 706. The target 210 may be used in other ways to serve as a basis for alignment (e.g. manually holding the target 210 in the center of the surgical volume). Once the sensor 202 is appropriately aligned with the surgical site, based on the pose of the target 210, the surgeon preserves this alignment by mechanically locking the sensor in place.

Once the sensor 202 is aligned (and the surgeon has advanced the software), and prior to hip dislocation, a baseline pose measurement is taken, as indicated in step 606. During the baseline measurement, the femur is held in a neutral position with respect to the pelvis. The baseline pose is stored in the memory of the workstation 218, for example, for accessing later in the procedure. At this point, the surgeon may advance the software and remove the sensor 202 (along with pelvic clamp 206, as well as target 210 (with beacon 214) and proceed with the surgery until they are ready to assess intra-operative leg length and offset, at which point the sensor 202 (along with pelvic clamp 206), as well as target 210 (with beacon 214) are replaced on the patient. In one example, the pelvic clamp 206 may be attached to a repeatable mechanical connection on the pelvic platform 208 and the beacon may be attached to a repeatable mechanical connection on the femur platform 216. At this time, as indicated in step 608, the surgeon is prompted to perform an RROM, which collects pose data from various pre-determined leg motions and/or positions. From this data, the current hip COR and patient's anatomical coordinate frame are extracted (for example, by fitting pose data to geometrical models, using well-known mathematical techniques). The anatomical coordinate frame will subsequently be used to express pose measurements in terms of leg length and offset, rather than an arbitrary coordinate frame associated with the sensor 202. The hip COR will subsequently be used to compensate for femur orientation when calculating leg length and offset change.

After the completion of the RROM, the software automatically advances, and the workstation 218 (via the GUI) begins displaying real time and continuous leg length and offset change measurements to the surgeon (step 610), as previously shown in FIG. 5. The leg length and offset change measurements compensate for the current orientation of the femur by considering the baseline femur orientation, as well as the hip COR as determined in step 608; the system 200 compares the baseline pose with the current (orientation-compensated) pose, and expresses the difference in the patient's anatomical coordinate frame, also determined in step 608. The surgeon has the option to manually capture the data (as in step 612), for example, via the user input associated with a "record" indicator 506. The surgeon has the option to end the program, as in step 614, which may trigger a surgical data log on the workstation, once they are pleased with the patient's leg length and offset. If there is a change in hip COR due to an acetabular side change (for example, changing liners, changing cup position, etc), the surgeon returns to step 608 to repeat the RROM procedure (for example, via the user input associated with a "back" indicator 508), in order to recalculate the hip COR. This is because the software compensates for femur orientation by "virtually rotating" it back to the baseline pose orientation, and uses the acetabular hip COR as the pivot point for virtual rotation. Rather than returning to step 608 to repeat the RROM procedure, since the patient's anatomical coordinate frame is not subject to change due to an acetabular COR positional change, an alternative method may include a step to calculate the new hip COR only (for example, by tracking the articulation of the reduced hip joint). In a further alternative embodiment, during step 610, the software may continuously estimate hip COR to automatically detect if a change in hip COR position has occurred. This may be accomplished by tracking poses during a reduction, and relying on the constraint that during a given hip reduction, leg length and offset change measurements should not change.

Since the system 200 is a surgical device, sterility of the system components within the sterile field is important. Conventional methods for achieving sterility include: terminal sterilization (i.e. a single-use disposable, sterilized with gamma radiation, ethylene oxide, etc), re-sterilization (via hospital processes, such as autoclaves), and barrier/draping (i.e. a protective sterile barrier covering non-sterile equipment). With regard to system 200, the following components are preferably either capable of re-sterilization, or are terminally sterile: beacon, femur platform, pelvic platform, pelvic clamp. Components such as bone screws and the target are well suited for terminal sterilization (to maintain their performance). The sensor may be terminally sterilized, and provided as a single-use disposable item, or re-used with a sterile drape. Some commercially available sterile drape products are intended to be used with endoscopic cameras, and provide an integrated optical "window". (One example of a commercially available drape is a Closed System Camera Drape (PN 96-5204) from Sklar Instruments, West Chester, Pa.) Such a drape may be preferred for use with a non-sterile sensor 202 since the drape accommodates cabling throughout, and facilitates optical sensing through the window, while maintaining a sterile barrier.

Where a sterile drape is used to maintain sensor sterility, the pelvic clamp may be configured to add another functional characteristic: to align the drape window with the sensor optics. In FIG. 8A, an exploded view of a pelvic clamp assembly 800 is shown with a sterile drape 804. Pelvic clamp assembly 800 consists of sensor 202 and pelvic clamp 206, and optionally a shroud 806 and a sterile drape 804 The sterile drape 804 maintains a sterile barrier between the non-sterile sensor 202 and the surgical field. The shroud 806 (sterile) clamps, or fixes the sensor 202 through the sterile drape 804, and an alignment feature 810 (e.g. a ring clip) of the shroud 806 is used to align a drape window 812 with the sensor's optical element 814. The shroud 806 (shown in a simplified manner) has an outer surface 816 which matches a mating surface on the inside of the clamp 818. Each of the mating surfaces may define portions of a sphere, such that the clamp/shroud interface provides an alignment mechanism that is functionally a lockable ball joint. The clamp 206 (sterile) has a mechanism (e.g. a screw/hinge combination) which applies a force on the shroud 806 (and, in turn, the sensor 202), and clamps it rigidly and releasably in place. Hence the shroud and the clamp have respective mating surfaces which, when the sensor is in the shroud and the clamp is in a partially closed position, enable relative movement of the shroud and clamp to adjust the orientation of the sensor.

On the clamp 206 there is a quick connection mechanism 820, which is used to repeatably couple the sensor 202 with the pelvis 204 via the pelvic platform 208.

As components of system 200, the sensor 202 and pelvic clamp 206 may be used as follows. The non-sterile sensor 202 gets transferred into the sterile drape 804, according to the standard sterile draping techniques for which the sterile drape 804 is intended. Next, by sterile personnel, the sterile drape window 812 is manually aligned with the sensor optical element 814. Next, the shroud 806 is engaged with the sensor 202 through the sterile drape 804, such that the shroud engages the sensor 202 so that the drape window 812 is held in place with respect to the sensor optical element 814, using the shroud's alignment feature 810. The sterile personnel may insert the assembly consisting of the shroud 806, sensor 202, and sterile drape 804 into the pelvic clamp 206, and perform an alignment or aiming procedure, as described in steps 304 and 604. The aiming may be performed manually, by grasping the back portion of the sensor 202 (exposed when inserted into pelvic clamp 206) and manipulating its orientation. The assembly of FIG. 8 meets the requirements of: sterility, ability to aim sensor 202 (in 3 degrees-of-freedom, due to the mating spherical surfaces) and lock the sensor 202 in place, maintaining optical performance, and providing a quick-connection mechanism to the pelvis.

In FIG. 8B, the pelvic clamp assembly 800 is shown in an assembled state. When assembled, the shroud mates with the drape window in such a way as to facilitate wiping (e.g. if debris ends up on the drape window, this could obscure the optics and interfere with operation of system 200).

Figure 9:
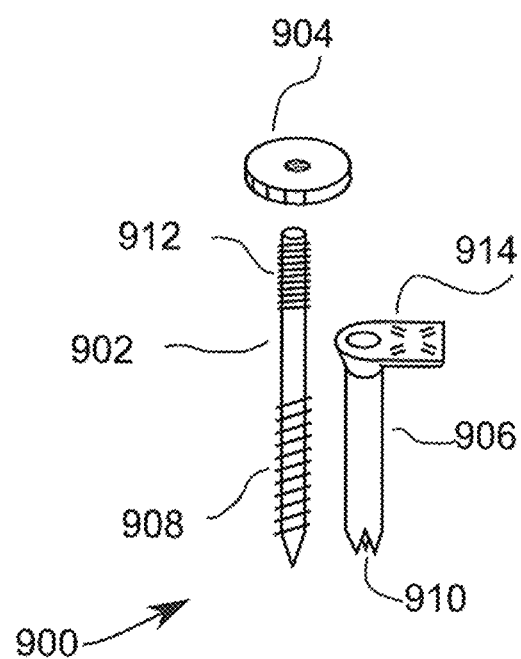
FIG. 9 shows components of a pelvic platform in accordance with an example.

An example pelvic platform 900 (an example of platform 208) is illustrated in FIG. 9. There are three subcomponents: a screw 902, a thumbnut 904, and a cannulated hub 906. The operation of this device is as follows. The screw gets driven into the pelvis, and the bone threads 908 engage with the bone. The cannulated hub slides down the shaft of the screw until the spikes 910 contact bone (alternatively, the cannulated portion may be used as a dilator or guide for the screw insertion). The thumbnut is advanced downward along the machine threads 912, until it cinches the cannula spikes 910 (or alternatively referred to as teeth) into the bone. This device provides very rigid fixation, including torsional rigidity, using only a single stab incision. On top of the cannulated hub, there is a repeatable quick connection mechanism 914 intended to mate with the pelvic clamp connection mechanism 820.

Figure 10:
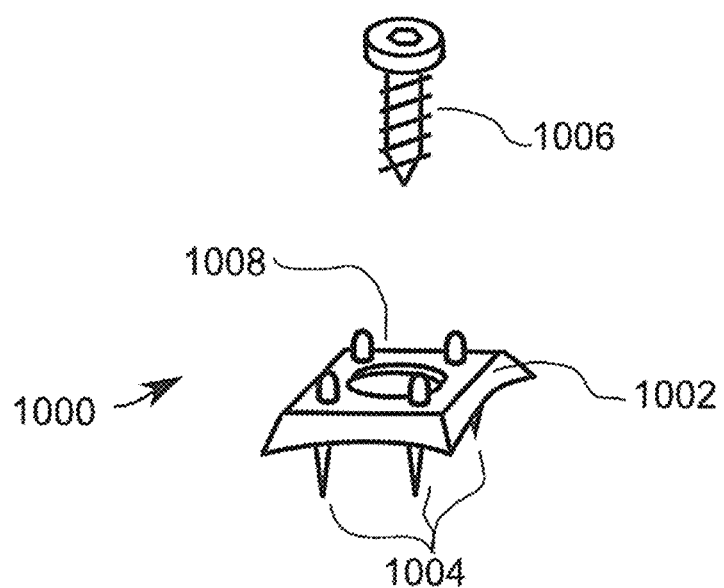
FIG. 10 shows a femur platform with femur screw in accordance with an example.

A femur platform 1000 (an example of femur platform 216) is shown in FIG. 10. The femur platform body 1002 is impacted into the femur (preferably the greater trochanter) and engages via the spikes 1004. Next, the femur screw 1006 is inserted through the femur platform body to cinch the assembly downward, and provide a very rigid structure. The screw length is such that it will not breach the femoral intra-medullary canal, which would interfere with the surgeon's broaching process during the THA. On the femur platform body, there is a quick connect mechanism 1008, which is used to connect the femur platform 1000 to a beacon 214, as described further below. The architecture of the femur platform is very similar to the pelvic platform—there is a bone screw which cinches down spikes to form a rigid structure with a quick connection mechanism.

Figure 11A:
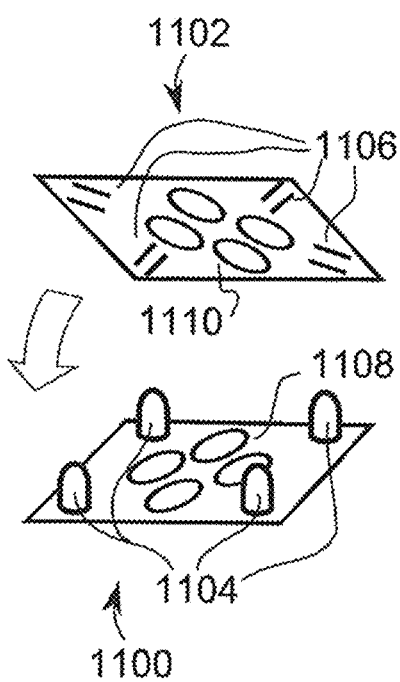
FIGS. 11A and 11B show an example quick connection mechanism.
Figure 11B:
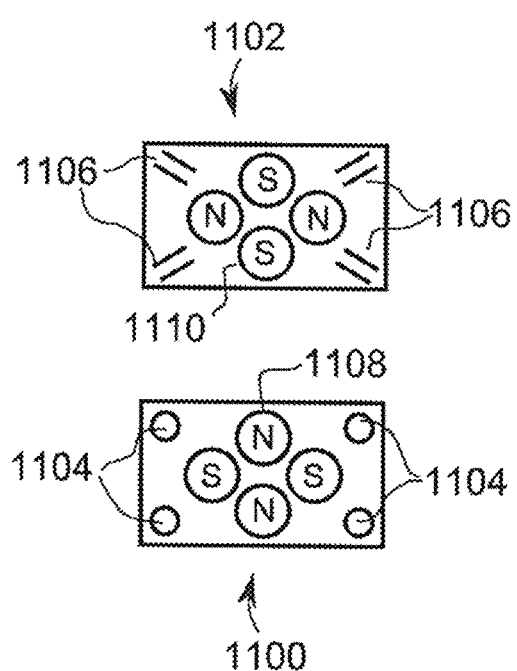

The quick connection mechanism (which interfaces the pelvic clamp 206 and pelvic platform 208 and the beacon 214 and femur platform 216) facilitates a clear, un-crowded surgical site by allowing for the respective components to be removed when not in use (leaving behind the unobtrusive pelvic and femur platforms). FIG. 11A illustrates the details of an example quick connection mechanism with an isometric view, and FIG. 11B illustrates the details of the example quick connection mechanism using a plan view. This example mechanism contains two mating components: a first side 1100 and a second side 1102. Both first side 1100 and second side 1102 mate via the combination of bull-nosed pins 1104 and rails 1106, which provide a very repeatable contact surface.

The bull-nosed pin is a pin which terminates hemispherically, and the rails provide two parallel contact surfaces which contact the pin on the hemispherical portion (i.e. the spacing between the rails is smaller than the diameter of the hemisphere). The rails 1106 may be implemented using dowel pins, or by machining slots, preferably chamfered, directly into the second side itself. Three pairs of bull-nosed pin 1104 and rails 1106 may be used for a repeatable connection; however, in practice, this arrangement may not provide sufficient stability, in which case, four pairs may be used (as shown), while maintaining repeatability through precise manufacturing tolerances. In addition to providing a highly repeatable interface, the bull-nosed pin/rail combination provides a clearance distance between the first side 1100 and second side 1102 of the quick connection; this is important for surgical applications, as debris (e.g. blood, soft tissues, bone fragments) may soil the quick connection mechanism. By maintaining a clearance between both sides, the repeatable connection will maintain performance in the presence of debris that would be typically encountered in surgery. Similarly, the bull-nosed pin and rail design is tolerant of debris, since the pins and rails share a very small contact surface.

In addition to aligning the two sides repeatably, the quick connection requires a force to keep the first side 1100 and second side 1102 engaged. Many types of features may accomplish this; for example, springs, mating threads, cam-locks, etc. In FIG. 11B, complementary magnets 1108 (on the first side 1100) and 1110 (on the second side 1102) are used to generate a coupling force. In the design shown, the magnetic polarity is such that the first side 1100 and second side 1102 will self-align when brought in close proximity to each other. Furthermore, the quick connection first side 1100 and second side 1102, including rails 1106 and bull-nosed pins 1104, but excluding the first side magnets 1108 and second side magnets 1110, are preferably made from non-magnetic material. In this case, the first side 1100 and second side 1102 will easily "snap" into place; this feature is very important to surgeon-users, who value simplicity of use and confidence via positive tactile/audible feedback. Note that the two halves may be positioned in only two orientations, 180 degrees from each other; this feature is important since it provides flexibility.

Figure 12:
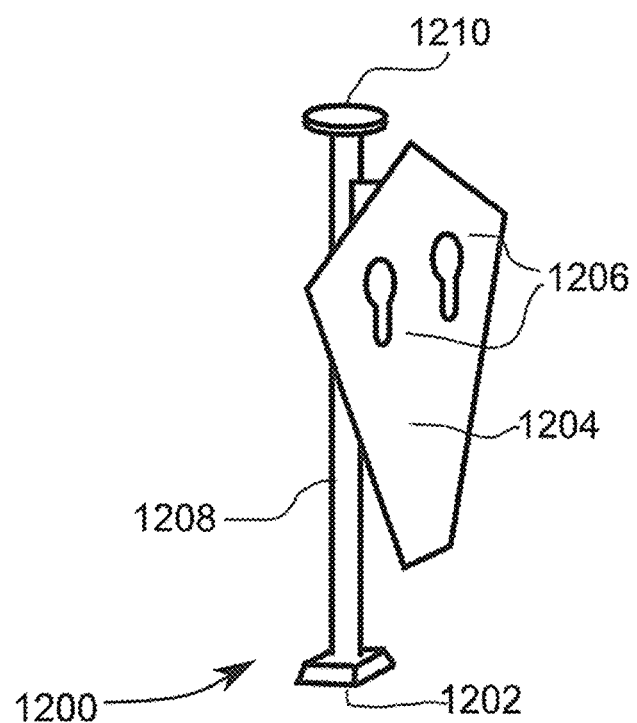
FIG. 12 shows a beacon component in accordance with an example.

A beacon 214 with a mating quick connect mechanism is intended to interface with the femur platform quick connection 1008 while rigidly holding the target 210. With reference to FIG. 12, a beacon 1200 is shown (an example of beacon 214) with a quick connection mechanism 1202 (in this case, a second side 1102) that interfaces with the femur platform quick connection 1008 (in this case, a first side 1100). The front face 1204 is a holder for the target 210, which indicates proper positioning of the target 210 by its shape (see FIG. 13). The holder 1204 has holding features 1206. The beacon 1200 provides a shaft 1208 which may be easily gripped by a surgeon for attaching to and detaching from the femur platform 216 without touching, and hence risking soiling, the target 210. A top of the beacon 1210 includes a surface capable of being impacted (e.g. hammered), which may be used to facilitate femur platform 1000 initial installation (i.e. to engage the spikes 1004, but prior to screw 1006 fixation). In summary, the beacon 1200 holds the target 210, and may be attached to and detached from the patient's femur (via femur platform 216) repeatably by the surgeon, as required for the purposes of using the system 200 for a THA.

Figure 13A:
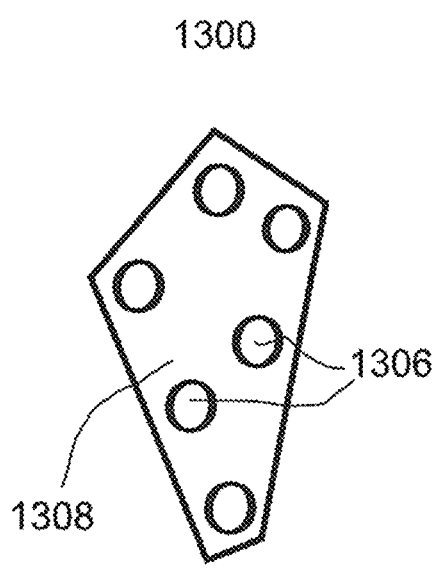
FIGS. 13A and 13B show respective front and back sides of a planar target, in accordance with an example, such as for mounting on beacon component of FIG. 12.
Figure 13B:
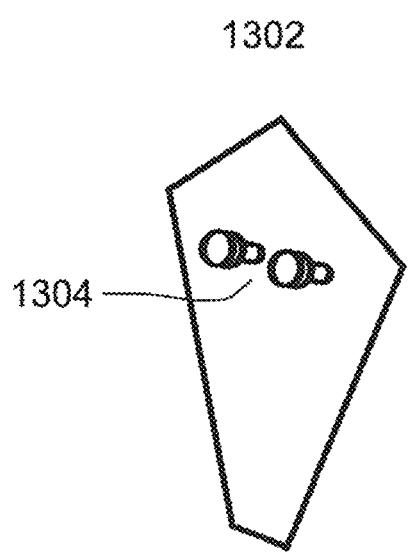

The target 210 provides a precise and identifiable pattern for pose tracking by the sensor during operation of system 200. Due to how the pattern is implemented and the precision required, the target 210 is preferably a disposable system component. FIGS. 13A and 13B show respective front 1300 and back 1302 sides of a planar target 210, in accordance with an example. The back of the planar target 210 includes an attachment mechanism 1304 used to secure the target to the beacon attachment mechanism 1206 (for example, in this case, a combination of slots and screws). The front of the target 210 has a pattern of markers 1306. The pattern of markers (which could include lines, circles, etc) may employ redundancy, such that if the target is partially occluded by debris (e.g. blood splatter), then the tracking system can still function. The markers 1306 are identifiable to the sensor 202 and may comprise a retro-reflective material (where the sensor 202 provides an illumination source). The markers are precisely positioned on the target substrate 1308. Positioning may be accomplished using a laser cutting procedure, due to the accuracy of laser cutting. In this manufacturing procedure, retro-reflective material is applied to cover the target substrate 1308. A laser cutter is used to kiss-cut the desired pattern (e.g. which may be loaded into the laser cutter via a CAD file). The excess retro-reflective material is weeded off, leaving behind the desired pattern. The target substrate 1308 may be of a black and diffuse material; in other words, the material is good for absorbing and scattering light, particularly in the wavelengths of the tracking system (e.g. such as near infra-red) so that the marker 1306 signals are easily identifiable relative to the substrate 1308 (e.g. the substrate does not cause specular reflections from the illumination of the sensor).

Figure 14:
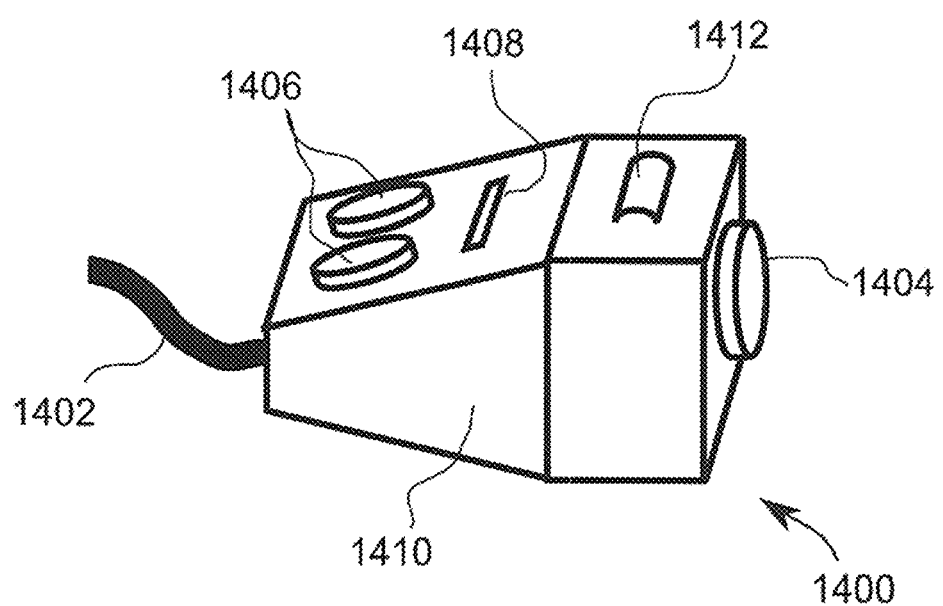
FIG. 14 shows a sensor in accordance with an example.

An example sensor 1400 (for example for use as sensor 202) is shown in FIG. 14. It communicates to the workstation 218 via a cable 1402, or alternatively, wirelessly. The sensor has an optical element 1404, which may include infra-red filters. Also, the sensor may include an integrated illuminator (not shown). The sensor contains a user interface, comprising user inputs (i.e. buttons) 1406 and a user indicator (i.e. indicator LED's) 1408. The user interface (both user inputs 1406 and user indicator 1408) maintains its function through a sterile drape 804. Having a user interface located within the sterile field is a significant advantage, particularly over conventional passive computer navigation products; the surgeon may interact with the software 220, rather than requiring verbal communication with non-sterile personnel. On the sensor enclosure 1410 there is a retaining feature 1412, for example, a ridge, (also on the bottom face of enclosure 1410), which is used to locate, or position the shroud 806, without the risk of compromising the sterile drape 804 barrier. Note that the enclosure 1410 also provides a locating feature (not shown) around the optical element 1404, for the shroud 806 to properly align the sterile drape window 812 with the optical element 1404. Internally, the sensor 1400 may store data in non-volatile memory, including calibration parameters, manufacturing information and information to maintain data integrity.

The sensor 1400 contains one optical sensor, which includes a lens, an imager, and possibly optical filters. Additionally, the sensor 1400 may include an illuminator, in the case of tracking a non-active target 210. Based on the sensor model (i.e. the camera calibration), and based on the art of monocular pose tracking, the sensor 1400 is able to provide the workstation 218 with sufficient sensor information to calculate the pose of a target 210, if the target 210 meets certain criteria (i.e. if the target 210 has a minimum of three identifiable features).

The workstation component can be any computing platform which can facilitate the necessary computations to translate sensor output into pose, and then further process the poses, as well as provide a graphical user interface.

It may be advantageous to deviate from, or supplement, the software workflow, as previously outlined in FIG. 6. A possible deviation would be to perform a RROM procedure contemporaneously with the baseline measurement 606. This would facilitate: determining a pre-operative hip COR and determining the patient's anatomical coordinate frame prior to trial reduction. The advantages of such an approach may include one or more of:

- obviating the need for the femur being neutrally positioned during baseline;
- facilitating acetabular cup positioning by tracking an impactor in anatomical reference frame (by coupling another target to the impactor);
- quantifying change in hip COR position (from postoperative to intra/post-operative).

Without performing an RROM contemporaneously with the baseline measurement, as suggested above, it is possible to position the acetabular cup under tracking guidance by repositioning the cup after the RROM procedure (FIG. 6, step 608). This may be done by starting with a trial cup, which is only loosely secured to the acetabulum, followed by a final cup, whose position is tracked via an additional target using the sensor 202, after the initial trial reduction. Similarly, the acetabular cup position may be verified after the RROM procedure, even if it is not practicable to change its position (e.g., if a final cup is impacted prior to RROM, its position can be verified). In any case, tracking the acetabular cup position may be done by attaching an additional target (a second target, or using the existing target 210) to the acetabular cup impactor in a known orientation.

It may be clinically beneficial to detect subluxation of the hip joint (an undesirable partial dislocation which occurs in certain orientations within the reduced range-of-motion). During step 610, the software and associated method may be modified such that subluxation can be detected and conveyed visually or audibly to the surgeon. This will allow surgeons to identify subluxation (which is often too subtle to detect by eye), identify where in the range of motion subluxation occurs, and then take corrective action. The premise is that system 200 compensates for femur orientation when calculating the leg length and offset change, by considering the location of the hip COR. As a result, in a given range of motion (i.e. without changing the size of the implants), the leg position will remain constant, no matter how the femur is oriented; therefore, if system 200 detects a change in a leg position measurement, the reason would be joint subluxation (in other words, the ball is at least partially coming out of the socket). The software 220 and method (step 610) could be modified to include a mode where, since the leg position should not change, apparent position changes are interpreted as joint subluxation, and conveyed to the surgeon. In one embodiment, the workstation 218 may alert in response to the detection, for example emitting an audible signal, or beep, when joint subluxation is detected during this mode. Using an audible signal would allow the surgeon to visually focus on the hip joint, and gain a clinical understanding of the nature of the joint subluxation.

In another embodiment, the system and method may be further modified to detect joint subluxation. For example, the pre-dislocation baseline pose measurement (in steps 304, 606) is not required to detect subluxation, meaning these steps may be omitted or modified accordingly. Similarly, calculating the map to the patient's anatomical coordinate frame (an objective of the RROM procedure) is not required to detect subluxation (although it may be useful to quantify where within the replaced hip range of motion subluxation occurs); however, it is preferable to calculate the hip COR. This is because the subluxation measurement fundamentally relies on checking whether the radius (in 3D space) of the target 210 position to the hip COR has changed within a given range of motion of a given reduced hip joint.

During step 610, a "cone of stability" may be generated by tracking the orientation of the femur at extremes of its range-of-motion and detecting poses where impingement or subluxation (as described above) may occur. This would allow the surgeon to assess whether the patient's range-of-motion is adequate (for example, a young, active patient may desire a large range of motion based on their day-to-day activities, whereas an elderly patient may not), and make clinical adjustments as necessary. The "cone of stability" can be generated and conveyed to the surgeon graphically, numerically, or in any other suitable manner. It is preferable for the "cone of stability" to be conveyed with respect to the patient's anatomical coordinate frame. The software 220 and associated method (step 610) may be modified to include a "cone-of-stability" mode, where the tracking system pose data is used to assess the artificial joint, particularly at extremes of the joints range of motion; furthermore, the information may be displayed to a surgeon via display 222, in the patient's anatomical coordinate frame.

Accordingly, it is to be understood that this invention is not limited to particular embodiments described, and as such may vary. It is also to be understood that the terminology used herein is for the purpose of describing particular embodiments only, and is not intended to be limiting.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

What is claimed is:

1. A navigational guidance system comprising:
an optical sensor to provide pose information for determining poses of a target, the target configured to couple to a rigid body, the rigid body comprising a bone, and the poses of the target indicating poses of the rigid body;
a sterile drape to drape the optical sensor to provide a sterile barrier, the sterile drape comprising an optically transparent window configured to align with the optical sensor;
a processing unit configured to:
determine a baseline pose for a first bone and a second bone using first pose information obtained from the optical sensor, the first bone and the second bone providing a baseline joint;
determine a reduction pose for the first bone and the second bone from second pose information obtained from the optical sensor, the first bone and the second bone providing a prosthetic joint;
determine a center of rotation for the first bone using third pose information obtained from the optical sensor, the third pose information for determining poses of the first bone through a range of motion; and
determine, and provide for presenting, the positional change between the first bone and the second bone using the baseline pose, the reduction pose, and the center of rotation.

2. The system of claim 1, wherein the first bone comprises a femur, the second bone comprises a pelvis, the baseline joint comprises a hip joint without a new implant, and the prosthetic joint comprises the hip joint including the new implant implanted by a procedure.

3. The system of claim 2, wherein the range of motion comprises a reduction range of motion for the prosthetic joint and the center of rotation provides a reduction center of rotation for the first bone in relation to the prosthetic joint.

4. The system of claim 3, wherein:
the processing unit is configured to determine a baseline center of rotation for the first bone in relation to the baseline joint using fourth pose information obtained from the optical sensor, the fourth pose information for determining poses of the first bone through a baseline range of motion in relation to the baseline joint; and
to determine the positional change between the first bone and the second bone further uses the baseline center of rotation.

5. The system of claim 2, wherein the range of motion comprises a baseline range of motion for the baseline joint and the center of rotation provides a baseline center of rotation for the first bone in relation to the baseline joint.

6. The system of claim 2, wherein the positional change comprises one or both of:
a difference in leg length comprising a difference between a baseline leg length and a reduction leg length; and
a difference in offset comprising a difference between a baseline leg offset and a reduction leg offset.

7. The system of claim 2, wherein to determine the positional change between the femur and the pelvis, the processing unit is configured to:
determine one of: i) an orientation-compensated baseline pose by virtually rotating the baseline pose about the center of rotation, the center of rotation providing a baseline center of rotation for the first bone in relation to the baseline joint; or ii) an orientation-compensated reduction pose by virtually rotating the reduction pose about the center of rotation, the center of rotation providing a reduction center of rotation for the first bone in relation to the reduction joint; and
determine the positional change as a difference between one of: i) the orientation-compensated reduction pose and the baseline pose; or ii) the orientation-compensated baseline pose and the reduction pose.

8. The system of claim 2 further comprising a platform configured to attach to the femur or the pelvis for repeatable coupling of the target.

9. The system of claim 2, wherein:
the new implant comprises a first implant; and
the processing unit is further configured to update, and provide for presenting, the positional change as updated for the prosthetic joint including a second implant replacing the first implant, the processing unit configured to determine the positional change as updated from further pose information obtained from the optical sensor.

10. The system of claim 1, wherein the optical sensor comprises a housing having a retaining surface configured to secure the optical sensor and the sterile drape in alignment with the optically transparent window.

11. The system of claim 1, wherein the processing unit is further configured to update, and provide for presenting, the positional change as updated in real time, determining, from further pose information obtained from the optical sensor, an updated reduction pose of the first bone and the second bone providing the prosthetic joint, and using the baseline pose, the updated reduction pose and the centre of rotation to update the positional change.

12. The system of claim 1, wherein the first bone and the second bone comprise bones of a human patient.

* * * * *